United States Patent
Staker

(10) Patent No.: US 9,359,641 B2
(45) Date of Patent: Jun. 7, 2016

(54) METHOD AND SYSTEM FOR ACCURATE ALIGNMENT AND REGISTRATION OF ARRAY FOR DNA SEQUENCING

(71) Applicant: Complete Genomics, Inc., Mountain View, CA (US)

(72) Inventor: Bryan P. Staker, San Ramon, CA (US)

(73) Assignee: COMPLETE GENOMICS, INC., Mountain View, CA (US)

( * ) Notice: Subject to any disclaimer, the term of this patent is extended or adjusted under 35 U.S.C. 154(b) by 0 days.

(21) Appl. No.: 14/309,049

(22) Filed: Jun. 19, 2014

(65) Prior Publication Data

US 2015/0080231 A1 Mar. 19, 2015

Related U.S. Application Data

(63) Continuation of application No. 13/092,618, filed on Apr. 22, 2011, now Pat. No. 8,774,494.

(60) Provisional application No. 61/330,130, filed on Apr. 30, 2010.

(51) Int. Cl.
*G06T 7/00* (2006.01)
*C12Q 1/68* (2006.01)
(Continued)

(52) U.S. Cl.
CPC ............... *C12Q 1/6874* (2013.01); *G06K 9/32* (2013.01); *G06K 9/42* (2013.01); *G06T 7/003* (2013.01);
(Continued)

(58) Field of Classification Search
CPC .......................................................... G06T 7/00
USPC ......................................................... 382/128
See application file for complete search history.

(56) References Cited

U.S. PATENT DOCUMENTS 6,210,891 B1 4/2001 Nyren et al.
6,272,207 B1 8/2001 Tang
(Continued)

FOREIGN PATENT DOCUMENTS

JP 2006-501807 A 1/2006
JP 2009-500004 A 1/2009
(Continued)

OTHER PUBLICATIONS

Comparison of Two Distance Based Alignment Method in Medical Imaging. G. Bulan, C. Ozturk. 2001.*
(Continued)

*Primary Examiner* — Stephen R Koziol
*Assistant Examiner* — Delomia L Gilliard
(74) *Attorney, Agent, or Firm* — Kilpatrick Townsend & Stockton LLP

(57) ABSTRACT

In a genome sequencing system and methodology, a protocol is provided to achieve precise alignment and accurate registration of an image of a planar array of nanoballs subject to optical analysis. Precise alignment correcting for fractional offsets is achieved by correcting for errors in subperiod x-y offset, scale and rotation by use of minimization techniques and Moiré averaging. In Moiré averaging, magnification is intentionally set so that the pixel period of the imaging element is a noninteger multiple of the site period. Accurate registration is achieved by providing for pre-defined pseudo-random sets of sites, herein deletion or reserved sites, where nanoballs are prevented from attachment to the substrate so that the sites of the array can be used in a pattern matching scheme as registration markers for absolute location identification. Information can be extracted with a high degree of confidence that it is correlated to a known location, while at the same time the amount of information that can be packed on a chip is maximized.

36 Claims, 20 Drawing Sheets

(51) Int. Cl.
*G06K 9/32* (2006.01)
*G06K 9/42* (2006.01)

(52) U.S. Cl.
CPC .............. *G06T 7/0012* (2013.01); *G06T 7/0026* (2013.01); *G06T 7/0044* (2013.01); *G06K 2209/07* (2013.01); *G06T 2207/10056* (2013.01); *G06T 2207/30072* (2013.01)

(56) References Cited

U.S. PATENT DOCUMENTS

| | | | |
|---|---|---|---|
| 6,309,824 B1 | 10/2001 | Drmanac | |
| 6,349,144 B1* | 2/2002 | Shams | G06T 7/0012 382/129 |
| 6,396,995 B1 | 5/2002 | Stuelpnagel et al. | |
| 6,401,267 B1 | 6/2002 | Drmanac | |
| 6,544,732 B1 | 4/2003 | Chee et al. | |
| 6,591,196 B1 | 7/2003 | Yakhini et al. | |
| 6,754,375 B1 | 6/2004 | Noblett et al. | |
| 6,828,100 B1 | 12/2004 | Ronaghi | |
| 6,833,246 B2 | 12/2004 | Balasubramanian | |
| 6,864,052 B1 | 3/2005 | Drmanac | |
| 6,873,422 B2 | 3/2005 | Nahum et al. | |
| 6,911,345 B2 | 6/2005 | Quake et al. | |
| 7,070,927 B2 | 7/2006 | Drmanac | |
| 7,072,500 B2 | 7/2006 | Cerrina et al. | |
| 7,230,705 B1 | 6/2007 | Yang et al. | |
| 7,323,681 B1* | 1/2008 | Oldham | G01N 21/6428 250/208.1 |
| 8,175,452 B1 | 5/2012 | Staker et al. | |
| 8,298,768 B2 | 10/2012 | Drmanac | |
| 8,445,194 B2 | 5/2013 | Drmanac | |
| 8,774,494 B2 | 7/2014 | Staker | |
| 2002/0102578 A1 | 8/2002 | Dickinson et al. | |
| 2002/0150909 A1 | 10/2002 | Stuelpnagel et al. | |
| 2002/0192650 A1* | 12/2002 | Amorese | B01J 19/0046 435/6.11 |
| 2003/0036067 A1 | 2/2003 | Schwartz et al. | |
| 2003/0219150 A1* | 11/2003 | Niles | G06K 9/00 382/128 |
| 2004/0056966 A1* | 3/2004 | Schechner | G06T 7/0018 348/229.1 |
| 2004/0264807 A1* | 12/2004 | Yakhini | G06K 9/00 382/289 |
| 2005/0049797 A1 | 3/2005 | Ghosh et al. | |
| 2006/0045314 A1 | 3/2006 | Gao et al. | |
| 2007/0087362 A1 | 4/2007 | Church et al. | |
| 2007/0207482 A1 | 9/2007 | Church et al. | |
| 2008/0171331 A1* | 7/2008 | Drmanac | C12N 15/66 435/5 |
| 2008/0213771 A1 | 9/2008 | Drmanac | |
| 2008/0234136 A1* | 9/2008 | Drmanac | C12Q 1/682 506/3 |
| 2009/0155793 A1 | 6/2009 | Oliphant | |
| 2009/0263802 A1* | 10/2009 | Drmanac | C12Q 1/6876 435/6.12 |
| 2009/0264299 A1 | 10/2009 | Drmanac et al. | |
| 2010/0093033 A1* | 4/2010 | Maizels | C07K 16/30 435/69.1 |
| 2012/0224050 A1* | 9/2012 | Staker | G01N 21/6452 348/95 |
| 2014/0085457 A1 | 3/2014 | Staker et al. | |

FOREIGN PATENT DOCUMENTS

| | | |
|---|---|---|
| WO | 03/064026 A1 | 8/2003 |
| WO | 2006/138257 A2 | 12/2006 |
| WO | 2009/059022 A1 | 5/2009 |
| WO | 2011/137183 A1 | 11/2011 |
| WO | 2012/031011 A1 | 3/2012 |

OTHER PUBLICATIONS

DNA Microarray Image Processing. Peter Bajcsy, Lei Liu and Mark Band. 2005.*
Drmanac et al., "Human Genome Sequencing Using Unchained Base on Self-Assembling DNA Nanoarrays" Science, vol. 327, No. 5961 (2010) pp. 78-81.
Extended European Search Report dated May 4, 2015 for European Patent Application No. 11 77 5531; 11 pages.
International Search Report and Written Opinion for PCT Patent Application No. PCT/US2011/50047 mailed on Jan. 5, 2012, 9 pages.
International Preliminary Report on Patentability for PCT Patent Application No. PCT/US2011/50047 mailed on Mar. 5, 2013, 7 pages.
International Search Report and Written Opinion corresponding to the PCT application No. PCT/US2011/034178, date of mailing Jul. 13, 2011,11 pages.
International Preliminary Report on Patentability for PCT Application No. PCT/US2011/034178, mailed on Nov. 15, 2012, 8 pages.
Bajcsy et al., *DNA Microarray Image Processing*, Aug. 26, 20005. [Retrieved on Jun. 24, 2011] Retrieved from the Internet: <URL: http://isda.ncsa.uiuc.edu/peter/publications/books/draftDNAPressChapter_v8.pdf>.
Potter, *A combinatorial approach to scientific exploration of gene expression data: An integrative method using Formal Concept Analysis for the comparative analysis of microarray data.* Thesis 2005, online [Retrieved on Jun. 25, 2011] Retrieved from the Internet: <URL: http://citeseerx.ist.psu.edu/viewdoc/download?doi=10.1.1.106.511&rep=rep1&type=pdf> abstract.
Gridline: Automatic Grid Alignment in DNA Microarray Scans. Peter Bajcsy, 2004 IEEE, 11 pages.
DNA Microarray Image Processing. Peter Bajcsy, Lei Liu and Mark Band, UIUC 2006, 77 pages.
Comparison of Two Distance Based Alignment Method in Medical Imaging. G.Bulan and C. Ozturk, IEEE 2001, 4 pages.

* cited by examiner

ALIGNMENT

ITERATIVE COARSE GRID FIT

```
for (θ = θmin ; θ <= θmax ; θ += Δθ){
for (S = Smin ; S <= Smax ; S += ΔS){
for (X = Xmin ; X <= Xmax ; X += ΔX){
for (Y = Ymin ; Y <= Ymax ; Y += ΔY){ calculate F(θ, S, X, Y)

}
}
}
} find minimum F
```

REGISTRATION

METHOD AND SYSTEM FOR ACCURATE ALIGNMENT AND REGISTRATION OF ARRAY FOR DNA SEQUENCING

CROSS-REFERENCES TO RELATED APPLICATIONS

The present application is a continuation of co-pending U.S. patent application Ser. No. 13/092,618 filed Apr. 22, 2011 and claims benefit under 35 USC 119(e) of U.S. provisional Application No. 61/330,130, filed on Apr. 30, 2010, entitled "Method And System For Accurate Alignment And Registration Of Array For DNA Sequencing," the contents of which are incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

This invention relates to imaging for biochemical analysis and more particularly to methods and systems for imaging high density biochemical arrays used in high-throughput genome sequencing.

High-throughput analysis of chemical and/or biological species is an important tool in the fields of diagnostics and therapeutics. Biochemical arrays allow multiple biochemical experiments to be performed in parallel. This ability accrues from the development of techniques to perform each experiment in a small volume and to pack the experiments closely together. Arrays of attached chemical and/or biological species on a substrate can be designed to define specific target sequences, analyze gene expression patterns, identify specific allelic variations, determine copy number of DNA sequences and identify, on a genome-wide basis, binding sites for proteins (e.g., transcription factors and other regulatory molecules). In a specific example, the advent of the human genome project required that 25 improved methods for sequencing nucleic acids, such as DNA (deoxyribonucleic acid) and RNA (ribonucleic acid), be developed. Determination of the entire 3,000,000,000 base sequence of the haploid human genome has provided a foundation for identifying the genetic basis of numerous diseases. However, a great deal of work remains to be done to identify the genetic variations associated with a statistically significant number of human genomes, and improved high throughput methods for analysis can aid greatly in this endeavor.

The high-throughput analytical approaches conventionally utilize assay devices, known as flow cells that contain arrays of chemicals and/or biological species for analysis. The biological species are typically tagged with multiple fluorescent colors that can be read with an imaging system.

Due to the sheer volume of data to be observed, captured and analyzed, a critical factor in genome sequencing analysis is the throughput of the assaying instrument. Throughput has a direct impact on cost. While imaging systems are capable of capturing a large amount of data as compared to other technologies, the throughput of such systems is limited by camera speed and number of pixels per spot. Camera speed is limited by inherent physical limitations, and the smallest number of pixels per spot is one. While it is desirable to reduce number of pixels per spot to a minimum, there are typically many pixels per spot in practical instruments.

Images captured in pixels from light emitted from spots associated with attachment sites on a substrate must be aligned and registered in order to be analyzable. The conventional registration technology, which involves registration marks and guides on the substrate, requires space on the substrate, reducing number of sites available for analysis and thus the volume of analysis per unit time.

Several different approaches to DNA chips are under development. In one approach a combinatorial array of DNA fragments is created on a chip and these are used for sequencing by hybridization. In another, DNA is randomly arrayed on a surface for the same purpose. One research group is trying to use arrays of DNA polymerase to observe sequencing base by base. Still another research group uses self-assembled DNA nanoarrays interrogated by combinatorial probe-anchor ligation. Although these approaches are quite different from one another, especially in their biochemical details, they all depend on fluorescence imaging techniques to literally "see" the data generated by individual experiments in an array.

Fluorescence imaging is used to identify DNA bases—A, C, G, or T—by designing biochemical reactions such that a different colored dye (for example, red, green, blue, or yellow) corresponds to each one. One may then observe a DNA experiment with a fluorescence microscope. The color observed indicates the DNA base at that particular step. Extracting data from a DNA chip thus depends on recording the color of fluorescence emitted by many millions or even billions of biochemical experiments on a chip.

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Diefenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, "*Oligonucleotide Synthesis: A Practical Approach*" 1984, IRL Press, London; Nelson and Cox (2000), *Lehninger, Principles of Biochemistry* $3^{rd}$ Ed., W. H. Freeman Pub., New York, N.Y.; and Berg et al. (2002) *Biochemistry*, $5^{th}$ Ed., W.H. Freeman Pub., New York, N.Y., all of which are herein incorporated in their entirety by reference for all purposes.

As used herein and in the appended claims, the singular forms "a," "an," and "the" include plural referents unless the context clearly dictates otherwise. Thus, for example, reference to "a channel" refers to one or more channels available on an assay substrate, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art upon reading the present disclosure that the present invention may be practiced without one or more of these specific details. In other instances, well-known features and procedures well known to those skilled in the art have not been described in order to avoid obscuring the invention.

Selected Definitions

"Amplicon" means the product of a polynucleotide amplification reaction. That is, it is a population of polynucleotides that are replicated from one or more starting sequences. Amplicons may be produced by a variety of amplification reactions, including but not limited to polymerase chain reactions (PCRs), linear polymerase reactions, nucleic acid sequence-based amplification, circle dependant amplification and like reactions (see, e.g., U.S. Pat. Nos. 4,683,195; 4,965,188; 4,683,202; 4,800,159; 5,210,015; 6,174,670; 5,399,491; 6,287,824 and 5,854,033; and U.S. Published Pat. App. No. 2006/0024711).

"Attachment site" or "site" herein refers to functionalized locations arranged in a regular pattern on a substrate to which bioactive structures can be bound. The sites in practice are submicron regions of reactive positive amines that are attached to an oxide surface via a silanization process.

"Circle dependant replication" or "CDR" refers to multiple displacement amplification of a circular template using one or more primers annealing to the same strand of the circular template to generate products representing only one strand of the template. In CDR, no additional primer binding sites are generated and the amount of product increases only linearly with time. The primer(s) used may be of a random sequence (e.g., one or more random hexamers) or may have a specific sequence to select for amplification of a desired product. Without further modification of the end product, CDR often results in the creation of a linear construct having multiple copies of a strand of the circular template in tandem, i.e. a linear, single-stranded concatamer of multiple copies of a strand of the template.

"Circle dependant amplification" or "CDA" refers to multiple displacement amplification of a circular template using primers annealing to both strands of the circular template to generate products representing both strands of the template, resulting in a cascade of multiple-hybridization, primer-extension and strand-displacement events. This leads to an exponential increase in the number of primer binding sites, with a consequent exponential increase in the amount of product generated over time. The primers used may be of a random sequence (e.g., random hexamers) or may have a specific sequence to select for amplification of a desired product. CDA results in formation of a set of concatemeric double-stranded fragments.

"Field" as used herein is a two-dimensional subunit of analysis, referring typically to the data captured by a camera and grouped together for the purpose of analysis.

"Grid" as used herein refers to an abstract Cartesian pattern which is employed to analyze location of information in an image constructed of pixels. The grid for the present purposes has constant periodicity in x and y and is preferably square. The location of the grid is conveniently specified in a pixel reference frame.

"Ligand" as used herein refers to a molecule that may attach, covalently or noncovalently, to a molecule on an assay substrate, either directly or via a specific binding partner. Examples of ligands which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles.

"Microarray" or "array" refers to a solid phase support having a surface, which in the present embodiment is necessarily a planar or substantially planar surface, which carries an array of sites containing nucleic acids such that each site of the array comprises many copies of oligonucleotides or polynucleotides, the sites being spatially discrete. The oligonucleotides or polynucleotides of the array may be covalently bound to the substrate, or may be non-covalently bound. Conventional microarray technology is reviewed in, e.g., Schena, Ed. (2000), *Microarrays: A Practical Approach* (IRL Press, Oxford).

"Nucleic acid" and "oligonucleotide" are used herein to mean a polymer of nucleotide monomers. As used herein, the terms may also refer to double stranded forms. Monomers making up nucleic acids and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like, to form duplex or triplex forms. Such monomers and their internucleosidic linkages may be naturally occurring or may be analogs thereof, e.g., naturally occurring or non-naturally occurring analogs. Non-naturally occurring analogs may include peptide nucleic acids, locked nucleic acids, phosphorothioate internucleosidic linkages, bases containing linking groups permitting the attachment of labels, such as fluorophores, or haptens, and the like. Whenever the use of an oligonucleotide or nucleic acid requires enzymatic processing, such as extension by a polymerase, ligation by a ligase, or the like, one of ordinary skill would understand that oligonucleotides or nucleic acids in those instances would not contain certain analogs of internucleosidic linkages, sugar moieties, or bases at any or some positions, when such analogs are incompatible with enzymatic reactions. Nucleic acids typically range in size from a few monomeric units, e.g., 5-40, when they are usually referred to as "oligonucleotides," to several hundred thousand or more monomeric units. Whenever a nucleic acid or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually nucleic acids comprise the natural nucleosides (e.g., deoxyadenosine, deoxycytidine, deoxyguanosine, deoxythymidine for DNA or their ribose counterparts for RNA) linked by phosphodiester linkages; however, they may also comprise non-natural nucleotide analogs, e.g., modified bases, sugars, or internucleosidic linkages. It is clear to those skilled in the art that where an enzyme has specific oligonucleotide or nucleic acid substrate requirements for activity, e.g., single stranded DNA, RNA/DNA duplex, or the like, then selection of appropriate composition for the oligonucleotide or nucleic acid substrates is well within the knowledge of one of ordinary skill, especially with guidance from treatises, such as Sambrook et al, Molecular Cloning, Second Edition (Cold Spring Harbor Laboratory, New York, 1989), and like references. As used herein, "targeted nucleic acid segment" refers to a nucleic acid targeted for sequencing or re-sequencing.

"Pixel" is an indivisible light sensing element of a camera reporting level of detected light at an indivisible location. A monochromatic pixel is a single photodetection element. Colors filters can be used to determine spectrum of light received at a pixel.

"Primer" means an oligonucleotide, either natural or synthetic, which is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers usually have a length in the range of from 9 to 40 nucleotides, or in some embodiments, from 14 to 36 nucleotides.

"Probe" as used herein refers to an oligonucleotide, either natural or synthetic, which is used to interrogate complementary sequences within a nucleic acid of unknown sequence. The hybridization of a specific probe to a target polynucleotide is indicative of the specific sequence complementary to the probe within the target polynucleotide sequence.

"Sequencing" in reference to a nucleic acid means determination of information relating to the sequence of nucleotides in the nucleic acid. Such information may include the identification or determination of partial as well as full sequence information of the nucleic acid. The sequence information may be determined with varying degrees of statistical reliability or confidence. In one aspect, the term includes the determination of the identity and ordering of a plurality of contiguous nucleotides in a nucleic acid starting from different nucleotides in the target nucleic acid.

"Spot" as used herein refers to the location of light emitted from a fluorescing molecule. A spot is not necessarily centered on an attachment site.

"Substrate" refers to a material or group of materials having a rigid or semi-rigid surface or surfaces. In the present context, at least one surface of the substrate will be substantially flat, although in other contexts not related to the present invention, it may be desirable to physically separate synthesis regions for different compounds with, for example, wells, raised regions, pins, etched trenches, or the like. According to other embodiments, the substrate(s) will take the form of beads, resins, gels, microspheres, or other geometric configurations. In the present invention, the surface of the substrate is limited to a planar structure to promote analysis.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the Tm value may be calculated by the equation. $T_m=81.5+0.41$ (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & Santa Lucia, J., Jr., Biochemistry 36, 10581-94 (1997)) include alternative methods of computation which take structural and environmental, as well as sequence characteristics into account for the calculation of $T_m$.

A conventional analysis slide consists of a 1"×3" silicon chip upon which arrays of functionalized sites are created. The sites are submicron regions of reactive positive amines that are attached to an oxide surface via a silanization process. The surrounding field consists of neutral, non-reactive methyl groups. The sites are arranged in 4.5 mm wide lanes down the narrow direction of the analysis slide. Currently a 19 mm×60 mm cover slip is bonded to the chip using glue. The glue forms lanes that are a maximum of 4.5 mm×19 mm. The spacing between the cover slip and the silicon slide is approximately 50 um. This 50 um space is maintained by adding 50 um glass beads into the glue.

The 19 mm width of the cover slip is substantially less than the maximum 25 mm width of the silicon slide because 5 mm is required for an entrance port. The entrance port is a region onto which pipettes dispense fluids onto the top of lanes. Capillary forces move reagents from the top of the lanes into the gap under the cover slip. At the bottom of the slide, 1 mm of additional distance is required to evacuate excess fluid.

There is a 1 mm to 4 mm keep-out region at the top and bottom of the lanes directly under the cover slip. This keep-out region is needed because of reagent evaporation, cover slip alignment accuracies and glue encroachment due to narrowed entrance ports. Taking into account all of these tolerances, the usable width of the analysis slide is about 12-15 mm of a total possible 25 mm in a conventional slide.

In a known design, twelve 4.5 mm lanes are constructed on an analysis slide. This yields a maximum usable width of 54 mm. However, 1 mm per lane is dedicated for glue lines. This gives a maximum usable width of only 42 mm. Fewer lanes could be fabricated, but this has been observed to destabilize the chip because of reduced bond line area and loss of alignment guides.

Given these dimensions, the overall useful percentage area of the chip of a conventional slide is approximately (12.5 mm×42 mm)/(25 mm×75 mm)=28%. What is needed is a design that provides increased usable area and a process that attains accurate alignment.

The following is a description of the analysis techniques under development in which the present invention is employed.

A promising approach to whole genome studies was recently introduced by a group from the assignee of the present invention led by Radoje Drmanac. ("Human Genome Sequencing Using Unchained Base Reads on Self-Assembling DNA Nanoarrays", Radoje Drmanac et al., *Science*, 327, p 78-81, Jan. 1, 2010 (which is not prior art under U.S. law). Combinatorial probe anchor ligation chemistry was used to independently assay each base from patterned nanoarrays of self-assembling DNA nanoballs. Three human genomes were sequenced with an accuracy of about one false variant per 100,000 bases. The high accuracy, low cost, and scalability of this platform enable complete human genome sequencing for the detection of rare variants in large-scale genetic studies.

Biochemical experiments in the Drmanac study were performed on rectangular chips measuring approximately 25 mm×75 mm. Each chip reportedly had approximately one billion DNA nanoballs arrayed on it in a regular, rectangular pattern. It is useful to visualize this array structure. FIG. 1 shows a conceptual diagram of such a biochemical array chip 100. Because of the vast number of nanoballs, the chip is divided conceptually into fields; e.g. field 105. A typical field size might be 0.5 mm×1.5 mm, although the exact size is not critical. Fields of manageable size enable imaging analysis to be performed in manageable chunks. In a step-and-repeat imaging system a field size may correspond to the system's field of view; in a continuous scanning system, the field size may be a convenient unit for data processing.

Referring to FIG. 2, a conceptual diagram is shown of a field 200 of a biochemical array chip. The field contains an array of spots (e.g., spots 205, 210, 215) where DNA sequencing experiments are performed. Although the field in FIG. 2 is drawn with only a few hundred spots, an actual field may contain approximately 10,000 to 1,000,000 spots. Inset 220 shows six spots from which fluorescence in any of four colors: blue ("B"), red ("R"), yellow ("Y"), and green ("G") can be observed. The actual colors used depend on the choice of fluorescent dye chosen and may be specified in terms of dye emission spectral data. The six spots shown in inset 220 correspond to data read out from six parallel DNA experiments, each reading a different spectrum. In this case, the fluorescence data indicate adenine ("A"), guanine ("G"), cytosine ("C"), and thymine ("T") as shown in inset 225.

It is intended that each site on a DNA chip contain a strand of DNA whose sequence is to be determined. The readout of inset 220 shown in FIG. 2 corresponds to a single step in determining the sequence of DNA in strands. The reading process is repeated many times.

It is important to keep track of exactly which spots on a chip one is looking at; otherwise the data obtained by recording fluorescence colors are meaningless. The field spots, i.e., the locations at which florescent dye molecules emit light, are nominally located in a regular, rectangular pattern. The actual pattern is not exact because DNA nanoballs do not always fall exactly on the centers of DNA attachment sites defined on the chip. The field spots are viewed with a camera whose image sensor contains a regular, rectangular array of light sensing pixels.

What is needed is a mechanism and methodology to maximize the informational content on a chip, provide registration targets, and provide control information for an imaging system in order to enhance throughput and thus improve sequencing proficiency.

SUMMARY OF THE INVENTION

According to the invention, in a genome sequencing system and methodology, a protocol is provided to achieve precise alignment and accurate registration of an image of a planar array of nanoballs subject to optical analysis. Precise alignment correcting for fractional offsets is achieved by correcting for errors in subperiod x-y offset, scale and rotation by use of minimization techniques and Moiré averaging. In Moiré averaging, magnification is intentionally set so that the pixel period of the imaging element is a noninteger multiple of the site period. Accurate registration is achieved by providing for pre-defined sets of sites, herein deletion or reserved sites, where nanoballs are prevented from attachment to the substrate so that the sites of the array can be used in a pattern matching scheme as registration markers for absolute location identification.

In a specific embodiment, DNA nanoballs self assemble themselves in the array at sites other than at the reserved sites, leaving a two-dimensional pattern of pseudo-random sites or micromarkers of deletion to which a corresponding mask (a mathematical template used for a cross correlation) can be used to register the array to an absolute location. Using minimization of two-dimensional spatial errors, scaling errors and rotational errors, and further applying Moiré averaging, alignment can be achieved with an extremely high degree of accuracy exceeding the optical resolution of the imaging optics in a best fit grid to the spots of light from the array of all DNA nanoballs in an image analysis field. Thus information can be extracted with a high degree of confidence that it is correlated to a known location, while at the same time the amount of information that can be packed on a chip is maximized.

In a specific embodiment, a deletion pattern comprises more than 1% and less than 3% of the array. The deletion spot locations are preferably chosen according a pseudo-random pattern to aid in absolute location registration. Localized registration is possible with regular deletion patterns, so long as the unambiguous range is less than the periodicity of the deletion pattern.

Other types of information are row/column identification patterns. Each field has a unique deletion pattern which identifies the field's position on a chip, which allows independent confirmation of the location of a field on a chip. Thus multiple deletion patterns are embedded in an array. Each of the deletion patterns is selected to be substantially orthogonal with one another.

In a specific embodiment, the fine alignment technique employs a Jacobian-based distance minimization methodology.

A primary purpose of this invention is to maximize the number of useable functionalized sites on a substrate so that the maximum amount of information can be extracted. Other purposes of the invention are to provide for a chip design that permits rapid analysis of elements at attachment sites, provides a high density of sites, minimizes reagent use, minimizes contamination, is mechanically robust, is sufficiently flat for imaging, is low cost, and is easily manufactured.

The invention will be better understood by reference to the following detailed description in connection with the accompanying drawings.

BRIEF DESCRIPTION OF THE DRAWINGS

FIG. 14 is a pseudo-code listing of the steps for an iterative coarse fit procedure.

DETAILED DESCRIPTION OF THE INVENTION

Figure 1:
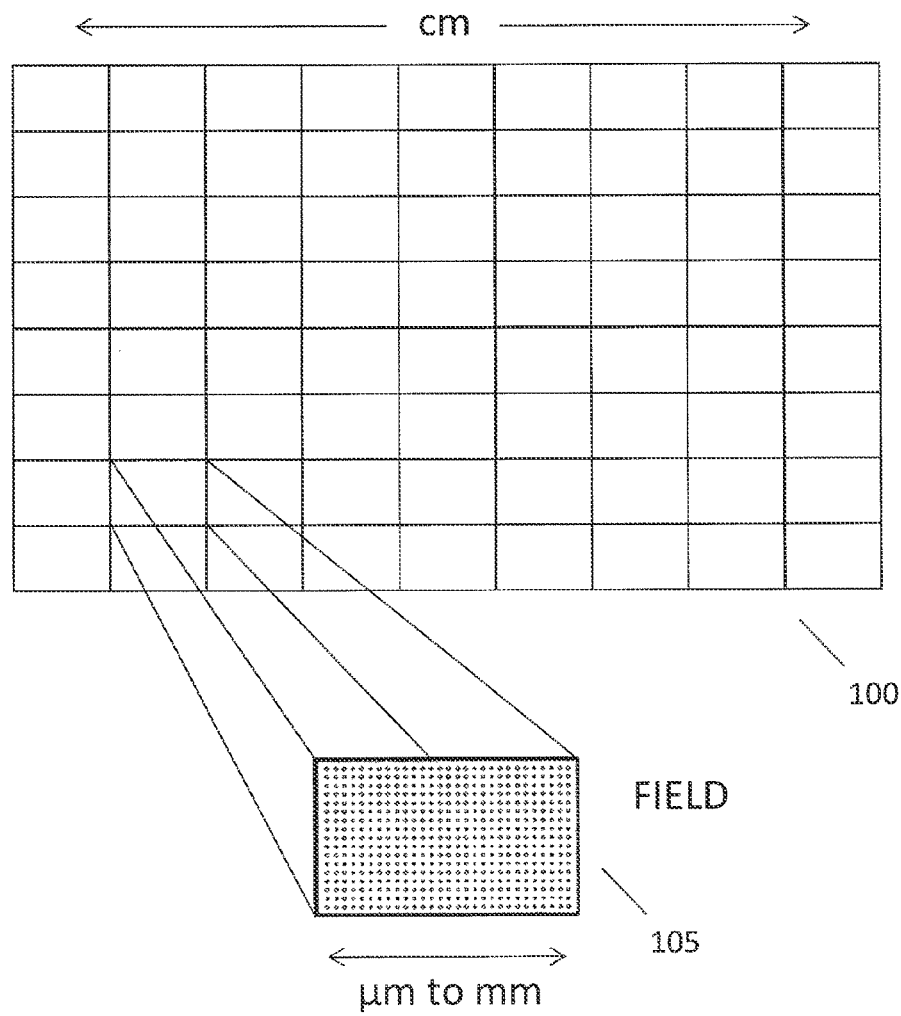
FIG. 1 is a conceptual diagram of a biochemical assay chip (prior art).
Figure 2:
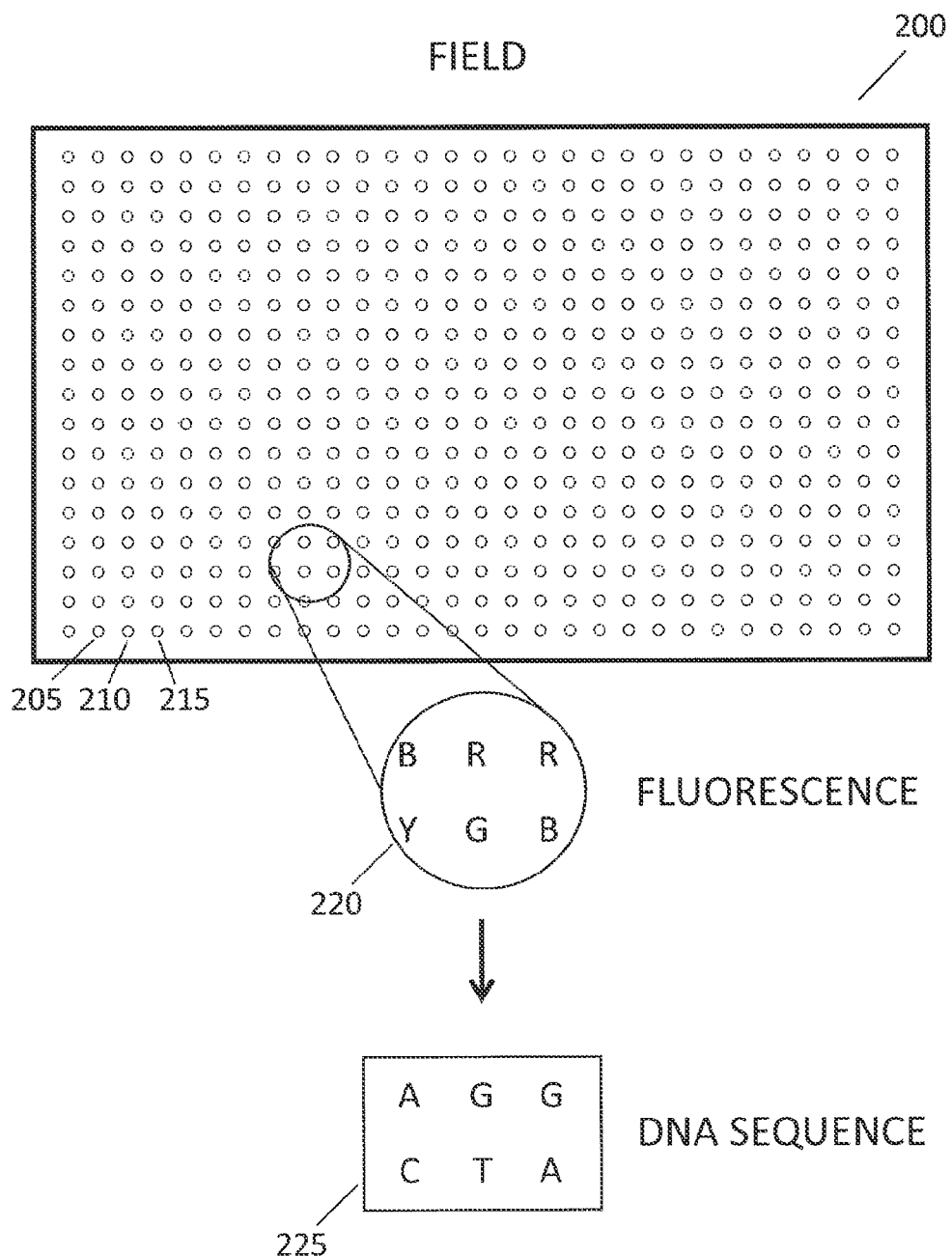
FIG. 2 is a conceptual diagram of a field of a biochemical assay chip (prior art).
Figure 3:
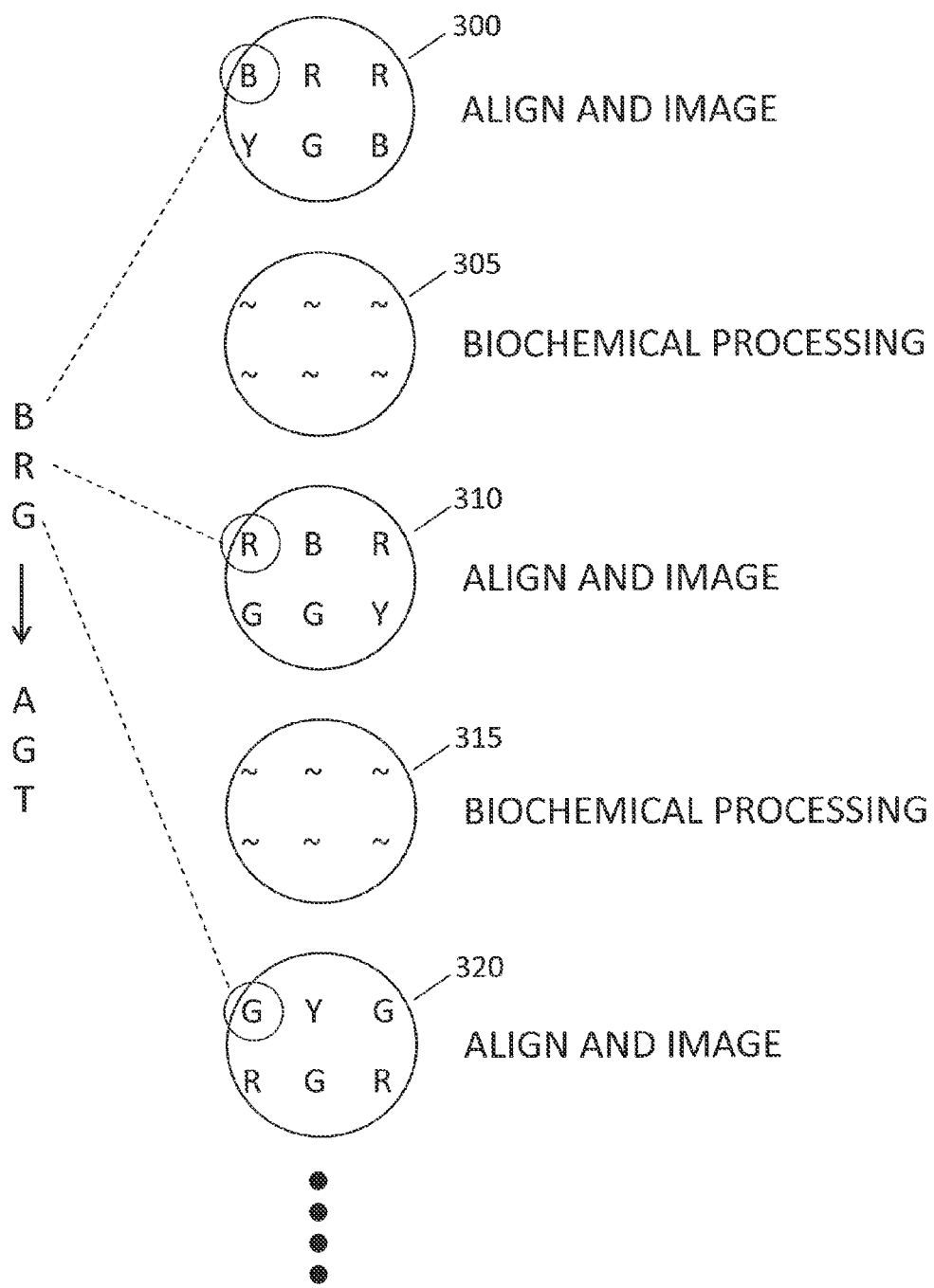
FIG. 3 is a conceptual diagram illustrating a two-tier process for imaging and biochemical processing in an array chip assay in accordance with the invention.

FIG. 3 is a conceptual diagram of imaging and biochemical processing steps used in an array chip assay, as hereinafter described. In FIG. 3, insets 300-320 are similar to inset 220 in FIG. 2 in that they show observations at a few spots on a chip. Insets 300, 310 and 320 show alignment and imaging steps in which fluorescence data are read out; insets 305 and 315 show biochemical processing steps that are performed between imaging steps. The sequence of DNA at one spot on a chip is determined by cycling imaging and biochemical processing steps. For example, in inset 300 one blue fluorescent spot "B" is circled. This same spot fluoresces red in inset 310 (circled "R") and green in inset 320 (circled "G"). Thus three cycles of imaging and biochemical processing at one spot reveal a fluorescence sequence "B R G" (blue, red, green), which for purposes of example is illustrated in FIG. 3 as corresponding to DNA sequence AGT (adenine, guanine, thymine).

Each "align and image" step in FIG. 3 may in fact involve acquisition of four images corresponding to the four dye colors used. In ultra high density systems, optics and detection equipment must be tuned for each wavelength to be detected.

When sequencing is performed on self-assembled DNA nanoball arrays using combinatorial probe-anchor ligation, biochemical processing steps (e.g. 305, 315) take significantly longer than alignment and imaging steps (e.g. 300, 310, 320). Chips are removed from the imaging apparatus during biochemical processing so that other chips can be imaged during that time.

Figure 4:
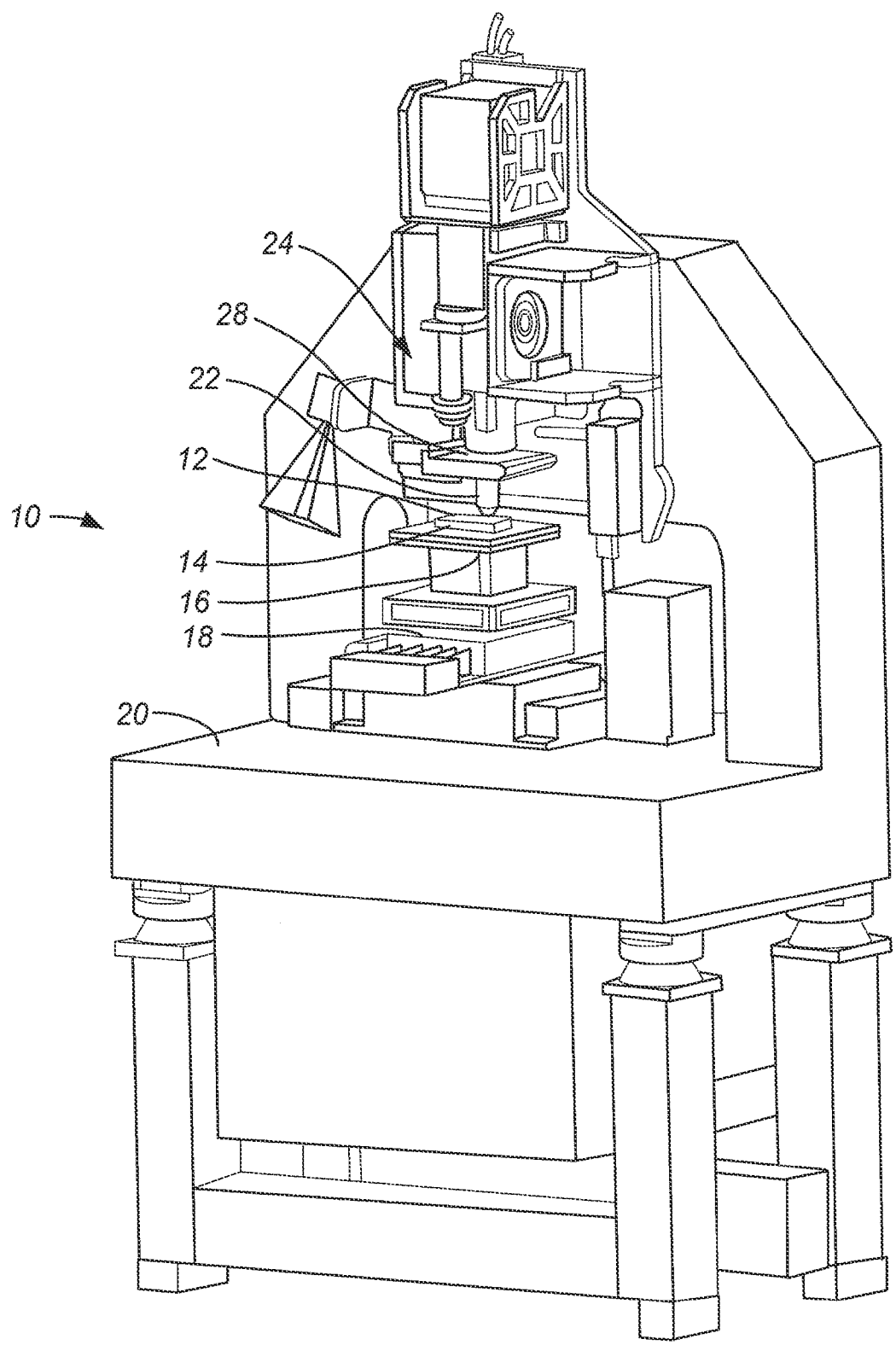
FIG. 4 is a perspective view of one embodiment of an assay system according to the invention.

FIG. 4 is an illustration of a representative assay system 10 showing a flow slide-having a functionalized silicon chip 12 upon which the DNA samples to be optically analyzed are mounted on a carrier 14 that is held by a vacuum chuck 16 supported upon a two dimensional translation stage 18 supported on a granite table 20. An objective lens 22 is disposed to observe the face of the silicon chip 12 and provide images to an imaging system 24 that feeds information to an alignment engine 26 (FIG. 6).

The imaging system 24 comprises a four-channel fluorescence detection system (not visible) where each channel measures the fluorescence of one of the types of bases of a strand of genetic material at each attachment site on the chip 12. The light emerges at a spot or a region with a peak of light from somewhere at the site. In the present case, measurements of the presence of T, G, C, & A (tyrosine, guanine, cytosine, and adenine) are made, respectively, with Fam, Cy3, Texas Red, and Cy5 dyes. A filter 28 for each color is moved into place and one image is snapped per color for a total of four images per field. The steps could be combined by using multiple imaging systems and multiple filters.

Figure 5A:
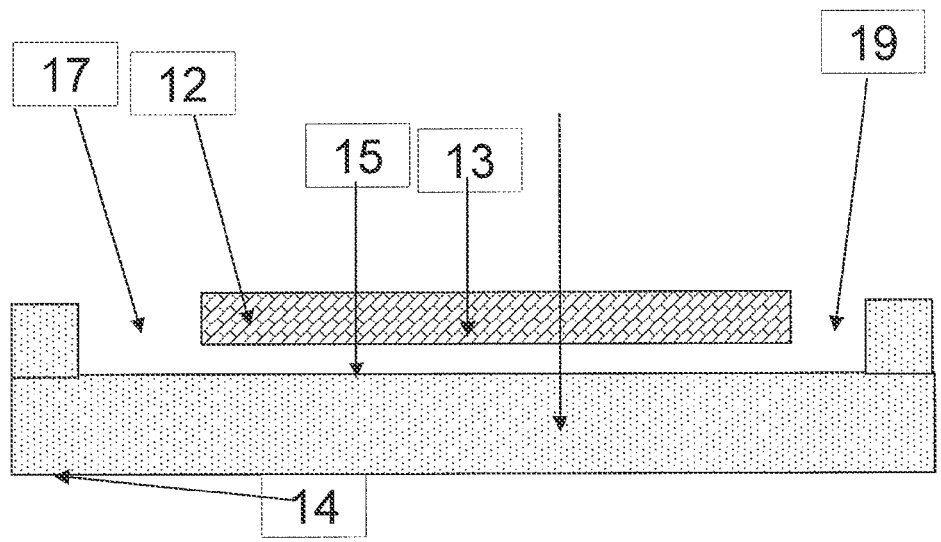
FIG. 5A is a side view of a representative top-side carrier for an assay chip.
Figure 5B:
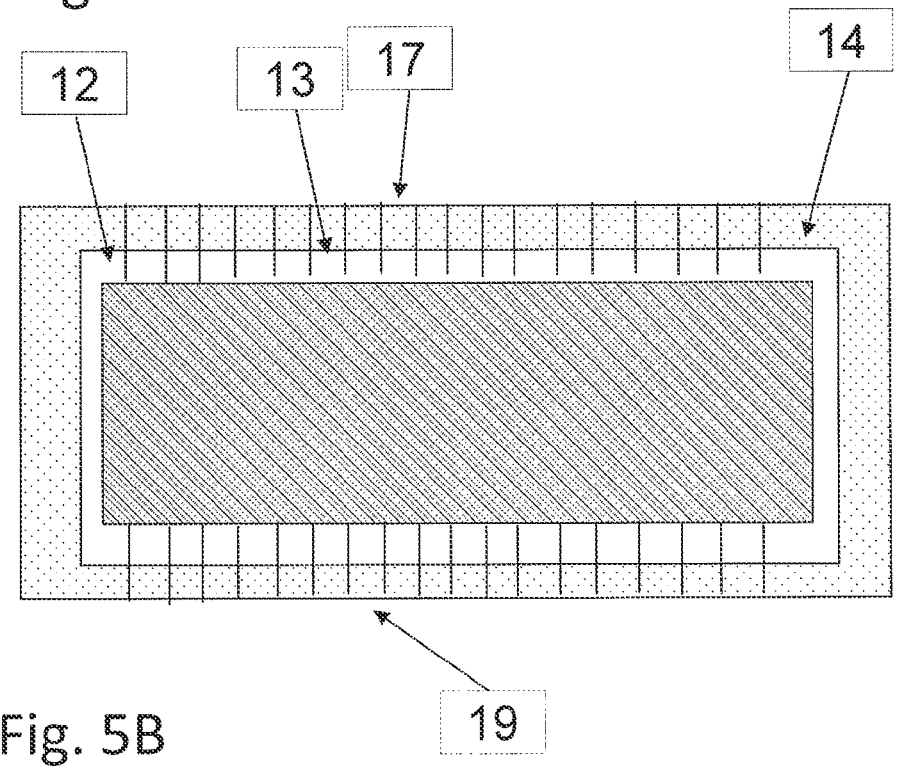
FIG. 5B is a top view of the carrier and assay chip of FIG. 5A.

Referring to FIG. 5A and FIG. 5B, a schematic illustration is shown of one embodiment of the carrier 14 upon which the chip 12 is mounted. In side view (FIG. 5A), illustrating one channel 13, the sample is on face 15, and fluid is accessible via an input port 17 and is drained from an output port 19. In the top view (FIG. 5B), it will be seen that there are a plurality of parallel channels like channel 13, each of which has a width that is substantially greater than the separation between the chip and the carrier. Other chip/carrier designs may be used, so long as there is a means to observe fluorescence of sites along the channels 13.

Figure 6:
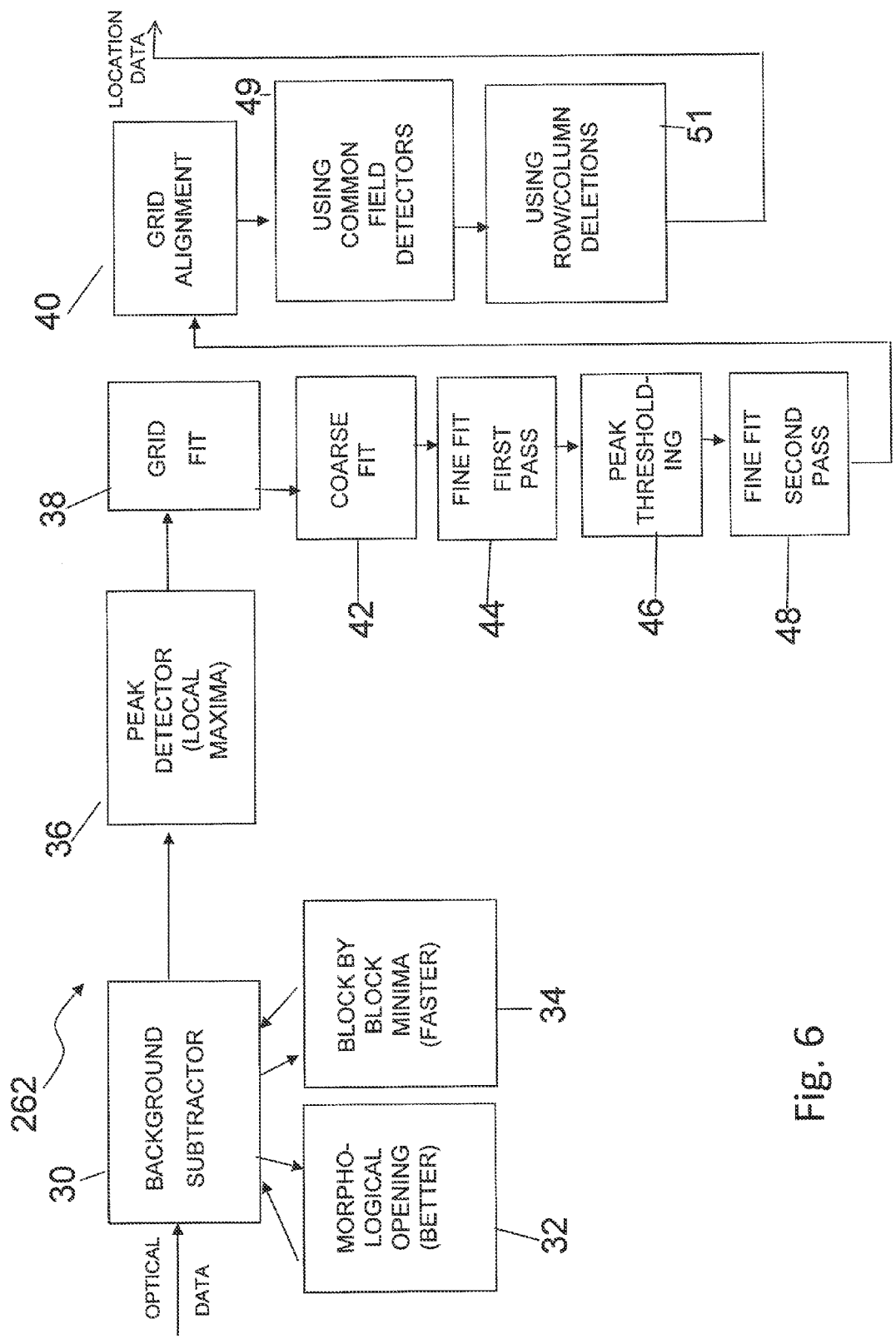
FIG. 6 is a functional block diagram of an alignment engine according to the invention.

Referring to FIG. 6, a suitable engine 26 is illustrated by functional elements used to perform the 2D alignment and registration process. The processes involved are further explained hereinafter, for example in connection with FIG. 11. The analysis engine 26 is operative to perform the three principal operations: first, capturing an image of the underlying pattern in the array, second, aligning the pattern, and third registering the image. As preparation for the process, and using as input the optical data from the patterned array of material on the chip 12, the patterned array is first characterized by a background mask that is used to delete noise. The dimmest sites are deleted from the analysis grid by a background subtractor 30, either by a process called morphological opening (element 32) or block-by-block minima (element 34). The morphological opening process is considered to be the more accurate but slower of the two processes, and it can be used alone or in combination with the other processes to attain the output of the background subtraction function.

Next, a two-dimensional peak detector 36 performs peak detection on small blocks of the pixels imaged from the chip 12 (see FIG. 12), typically in arrays of 5 by 5 or 3 by 3 to optically identify local maxima of fluorescence to collect useable data. The small blocks may overlap as the objective is stepped across and along the X and Y axes of the chip 12.

Thereafter the grid alignment subsystem 38 is activated. It is helpful to understand the factors that underlie the operations of the grid alignment subsystem 38. The first operation, creating the grid patterns to fit images of the chip 12, is subject to four primary degrees of freedom: scale, rotation, and X and Y offsets, as hereinafter explained. In the presence of astigmatism or distortion in the optics, more degrees of freedom may be included. Astigmatism results in different scale factors between the X axis and the Y axis of the grid. Radial magnification variation is one of several possible distortions. Each additional degree of variation will add a certain amount of uncertainty in the other axes. Each additional degree of freedom will also be costly in terms of analysis time, so only four degrees of freedom are generally used. There are typically four nested processes in the grid alignment process. First is a coarse fit 42 wherein a brute-force parameter sampling is performed to quickly and roughly fit the grid to the spots. Second is a first-pass fine fit 44 where there is an analytical optimization of the fit obtained in the coarse fit 42. Thereafter, the data is subjected to a peak thresholding process 46 to qualify additional candidate spots for processing, as hereinafter explained. Thereafter is a second-pass fine-fit analytical optimization 48 to fine tune the grid alignment 38.

The second operation is performed by a grid registration subsystem 40, to the end of registering the grid pattern so that the registration is absolute. In this operation, the location of the grid pattern in the image is found. The object is to identify which grid pattern has been imaged. This is accomplished by looking at site occupancy. As hereafter explained there are two types of site occupancy tests performed based on deletion patterns: using common grid deletions among all fields 49 and using row/column deletions 51 to identify the row and column of the specific grid.

Thus the four processes involved in the foregoing 2D alignment and registration engine are: (1) background subtraction, (2) peak detection, (3) grid alignment, and (4) grid registration. They are explained in greater detail hereafter.

Background Subtraction

Background subtraction is a necessary process to suppress stray light. Stray light in a fluorescent system may have gradients. These gradients may be a consequence of imperfections and blotches on the flow slide. Thus background subtraction is always necessary.

There are a number of different methods of background subtraction. Images are stored as intensities and negative numbers are not allowed. Background subtraction generally consists of finding the minimum intensity pixel in a region and calibrating on its intensity. The simplest technique is a block background subtraction wherein the intensity of the minimum pixel is found in a small sub-region. A method that gives slightly better results is a morphological background process that finds the minimum pixel in a region, where the region is defined as a window scanned across the image. It is slower than block subtraction, as it requires much more computation time. Other background subtraction methods may be used.

Peak Detection

Peaks are found by identifying pixels that are the maximum on either a 3×3 or 5×5 area, or on a greater area defined by (2n+1×2n+1) where n=1, 2, 3, 4, . . . . The size of the filter chosen is a function of the intrinsic pitch of the grid and the size of the spot under consideration. For present purposes, the pitches are <=4 pixels per spot and the spot sizes occupy 1-10 pixels, so the 3×3 and 5×5 grids are preferred.

Grid Alignment

Aligning the grid pattern makes use of the features of a Jacobian transformation. This is illustrated by the fitting the abstract grid 405 of points to a real field 400 of spots.

Figure 7:
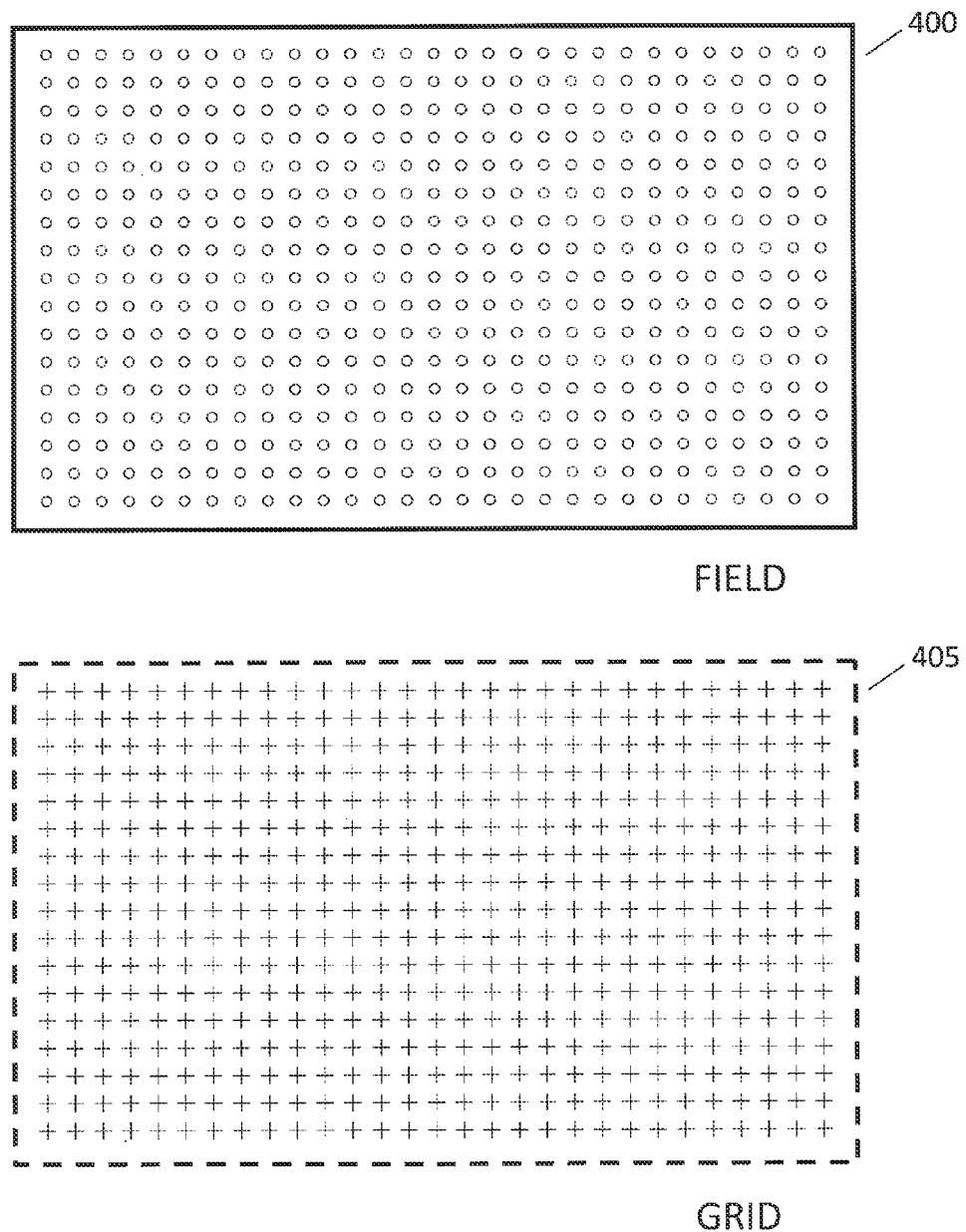
FIG. 7 is a conceptual diagram showing a real field and an associated analytical grid used for alignment determination.

Referring to FIG. 7, to aid in keeping track of field spots, an abstract grid 405 is used. The grid represents the coordinates of an ideal array that fits the pattern of field spots of a field 400 as closely as possible. The grid is ideal in the sense that it is exactly square and has constant periodicity.

Figure 8A:
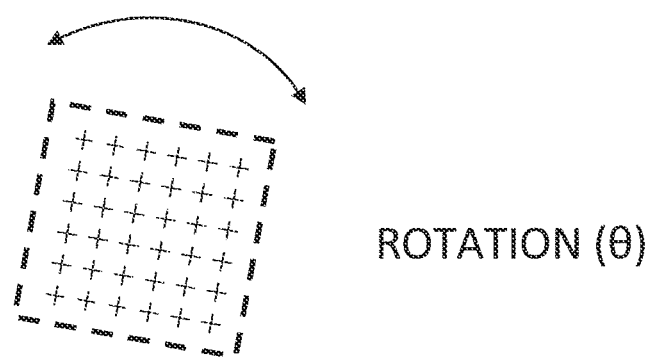
FIGS. 8A, 8B and 8C are diagrams for illustrating rotation, scale and offset.
Figure 8B:
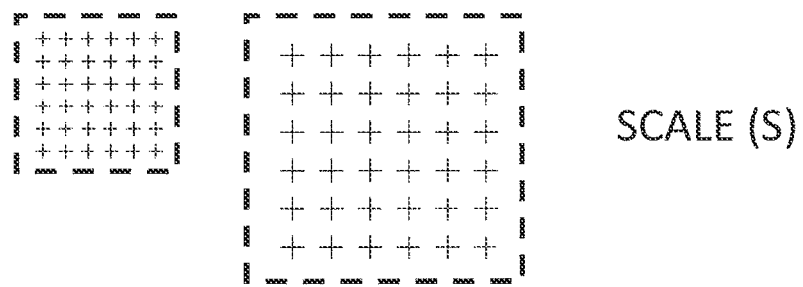
Figure 8C:
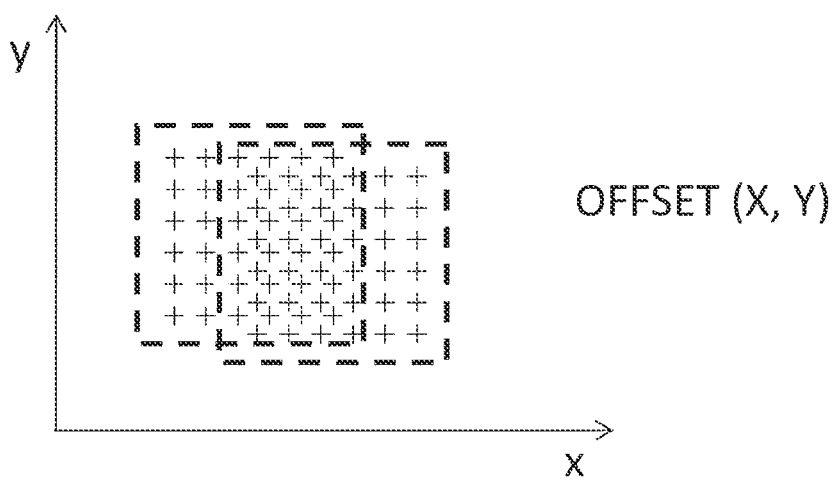

It is useful to know exactly where the grid is located in the pixel reference frame since the only observable quantities are pixel intensities at the image sensor. FIGS. 8A, 8B and 8C, respectively illustrate the concepts of grid rotation error, grid scale error, and grid offset error. Finding the grid location is a process that involves reducing these errors as much as possible. Rotation errors occur when the field and the grid are rotated with respect to each other as in FIG. 8A. Scale errors occur when grid has a periodicity different from that of the field, as in FIG. 8B. Offset errors occur when the grid is displaced in-plane; e.g., in the X or Y directions as shown in FIG. 8C. One type of offset error is an offset of less than half the distance between grid points. A second type of offset error, known as a registration error, is an offset of an integer number of grid periods.

Figure 9:
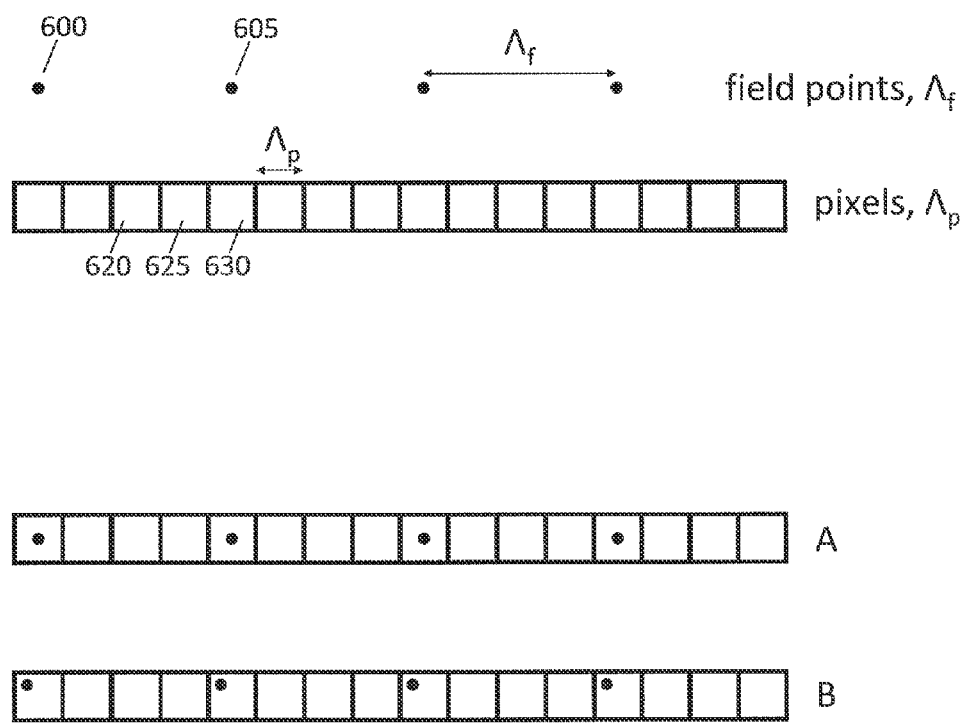
FIG. 9 is a diagram showing one-dimensional field-spot-to-pixel alignment for explanation of the need for Moiré averaging.

One fits the grid points to the field spots, while viewing is only via discrete camera pixels, since the field spots are not viewable at infinitely fine resolution. A careful choice of the ratio between the period of the field spots and the period of the camera pixels, so that integer relationships are avoided, increases the accuracy of the grid alignment operations. First consider a one-dimensional example of imaging field spots when the field period is an integer multiple of the pixel period as shown in FIG. 9. In FIG. 9, a line of field spots, including spots 600, 605, etc., has a period, or spacing between spots, $\Lambda f$. A line of camera pixels, including pixels 620, 625, 630, etc., has a period of $\Lambda p$. In the example of FIG. 9, $\Lambda f = n\Lambda p$, where n is an integer. Consider observing the line of spots with the line of pixels. In image "A" the spots are aligned in the centers of the pixels. In image "B" the spots are aligned in the upper left corners of the pixels. However, it is not possible to distinguish between images "A" and "B" using only pixels. A pixel cannot determine where light falls upon it. Thus in the example of FIG. 9 the pixels, and therefore a grid, could be misaligned by as much as 0.707 $\Lambda p$ and it would be difficult to detect the error.

Figure 10:
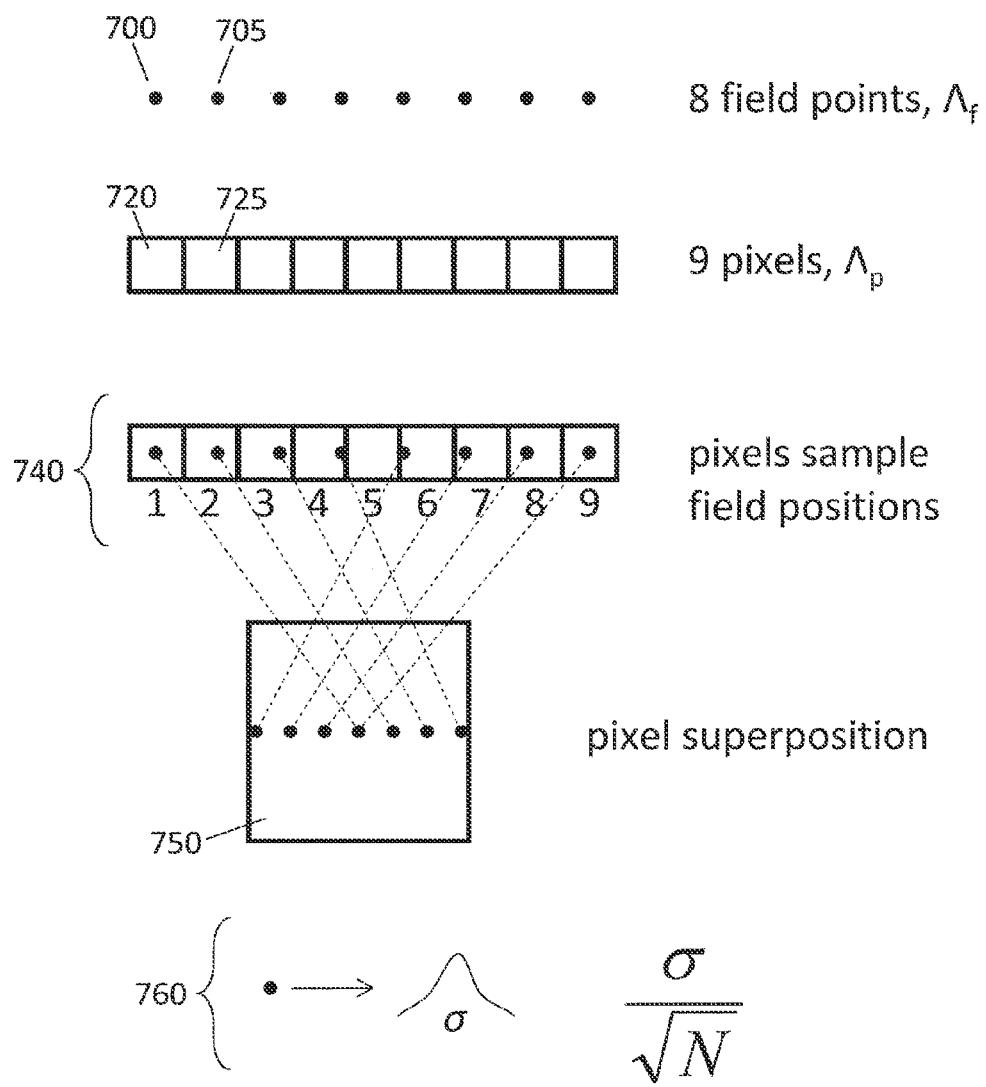
FIG. 10 is a diagram for illustrating advantages of Moiré averaging.

One solution is to choose a field (and grid) period that is not an integer multiple of the pixel period, as shown in the conceptual, one-dimensional example of imaging field spots of FIG. 10. In FIG. 10, a line of field spots, including spots 700, 705, etc., has a period, or spacing between spots, $\Lambda_f$. A line of camera pixels, including pixels 720, 725, 730, etc., has a period of $\Lambda_p$. In the example of FIG. 10, $8\Lambda_f = 9\Lambda_p$ (equivalently, $\Lambda_f = 1.125 \Lambda_p$). Consider observing the line of spots with the line of pixels as shown at 740 where the pixels are labeled "1" through "9". The field spots 1 and 9 and pixel 1 and 9 show that there is exact alignment only at every ninth pixel. The relative positions of the spots and pixels sweep through each other in the intervening pixels. Box 750 is a magnified view of pixels "1" through "9" superposed upon each other. The spots are spread evenly across the magnified superposed pixel. The difference in spot and pixel periods has led to the spots sampling the length of the pixel in equal steps. The average of all the spot locations in superposition 750 leads to an estimate of the best fit field location (i.e. the grid location) whose error is reduced by a factor $$\frac{1}{\sqrt{N}}$$

where N is the number of pixels between repeats; N=9 in this example.

As is evident, field spots do not have infinitesimally small extent, but in reality light is emitted in a spatial distribution. Ideograph 760 shows the generalization from point light sources to sources having a Gaussian extent characterized by standard deviation $\sigma$. In that case the error of fit that may be achieved is proportional to $$\frac{\sigma}{\sqrt{N}}.$$

Choosing a field (and grid) period that is not an integer multiple of the pixel period allows grid fitting with sub-pixel resolution. FIGS. 9 and 10 illustrate only a one dimensional example of creating intentional Moiré patterns between field arrays and pixel arrays. In an actual system, the same principle is applied in two dimensions. However, the benefit of two dimensional Moiré patterns is greater than simply sequential application of perpendicular one-dimensional Moiré patterns.

In superposed pixel 750 the sampled field spot positions lie on a line crossing the pixel from left to right. Applying the Moiré principle in the perpendicular direction, but performing two separate (e.g., X and Y) fitting procedures would lead to spots sampling the pixel in a line as shown and along a perpendicular line. However, as seen below, two-dimensional grid fitting involves minimizing the squared distance (e.g., $\Delta x^2 + \Delta y^2$) between grid locations and field spots in one step rather than minimizing X and Y errors separately. When squared distance is the minimized quantity, the whole superposed pixel area is sampled.

In the example of FIG. 10, field spots and pixels line up every nine pixels, thus defining a Moiré fringe or beat period. The number of fringes seen in one field is usually chosen to be roughly 10 to 20. The straightness of fringes may be used to detect field distortions.

Figure 11:
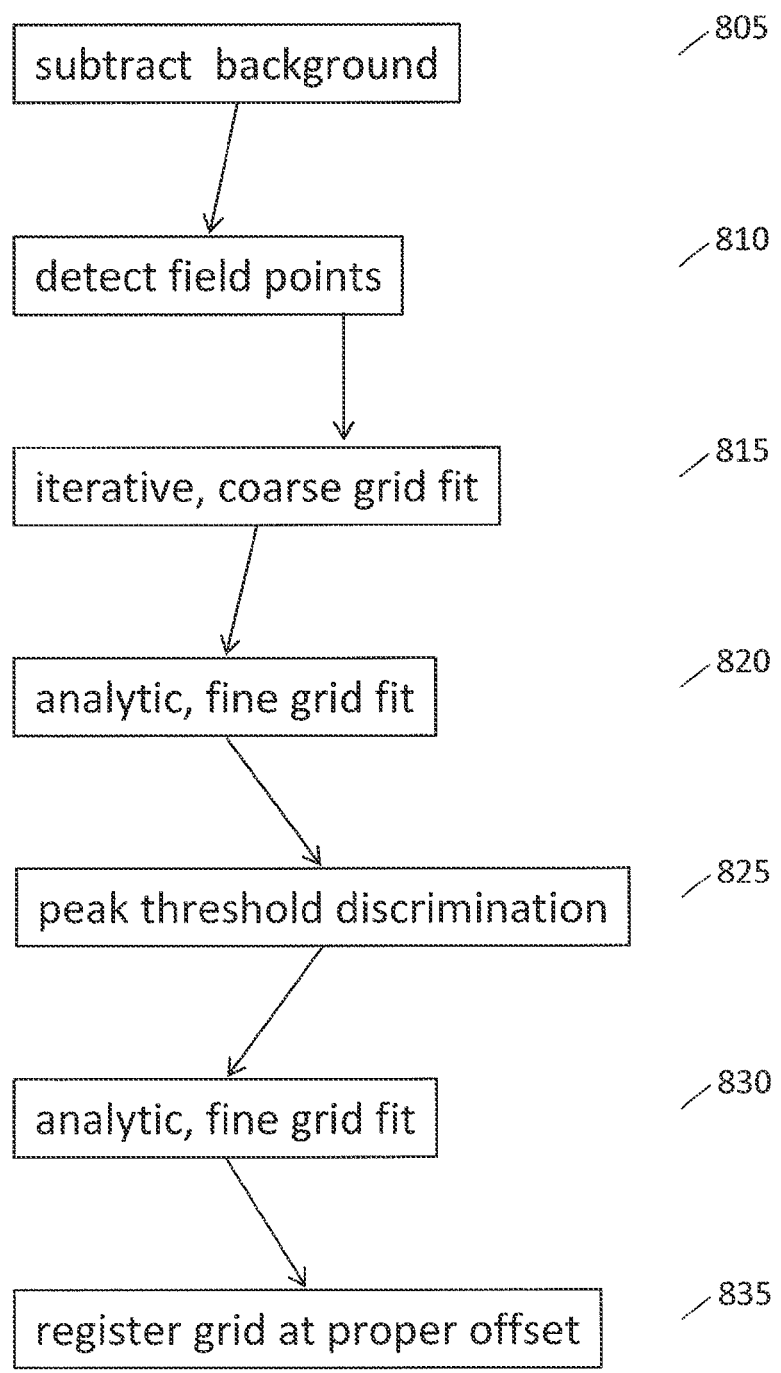
FIG. 11 is a basic flow chart for the alignment system of FIG. 6.

A result of a procedure for fitting a grid to a field as accurately as possible in two dimensions is a regular, rectangular grid that is fit to an observed field in the coordinate system of pixels in a camera image sensor. FIG. 11 shows steps in a grid alignment and registration procedure that is employed in the system according to the invention and corresponds to the engine of FIG. 6. In FIG. 11, steps 805, 810, 815, 820, 825, 830, and 835 are normally performed in the order shown; however, the order of steps is not a requirement for the procedure. Furthermore, not all steps are needed in all situations; therefore some of the steps may be omitted. For example, not all situations require peak thresholding discrimination 825 and fine grid fit 830, e.g., when high accuracy is not required.

Beginning with an image of a field as recorded by an image sensor in a camera, step 805 is subtracting background signal levels from the image. Step 810 is detecting field spots; i.e. finding where signals emitted by fluorescent dyes appear in the image. Step 815 is performing a coarse grid fit to the field spots using an iterative procedure. Step 820 is performing a fine grid fit to the field spots using an analytic procedure. In step 825 field spots are re-qualified by peak threshold discrimination. Step 830 is a second fine grid fit to the field spots using an analytic procedure that is performed on the re-qualified field spots. Step 835 is registering the grid at the proper offset; in other words, correcting for any modulo grid period errors.

Figure 12:
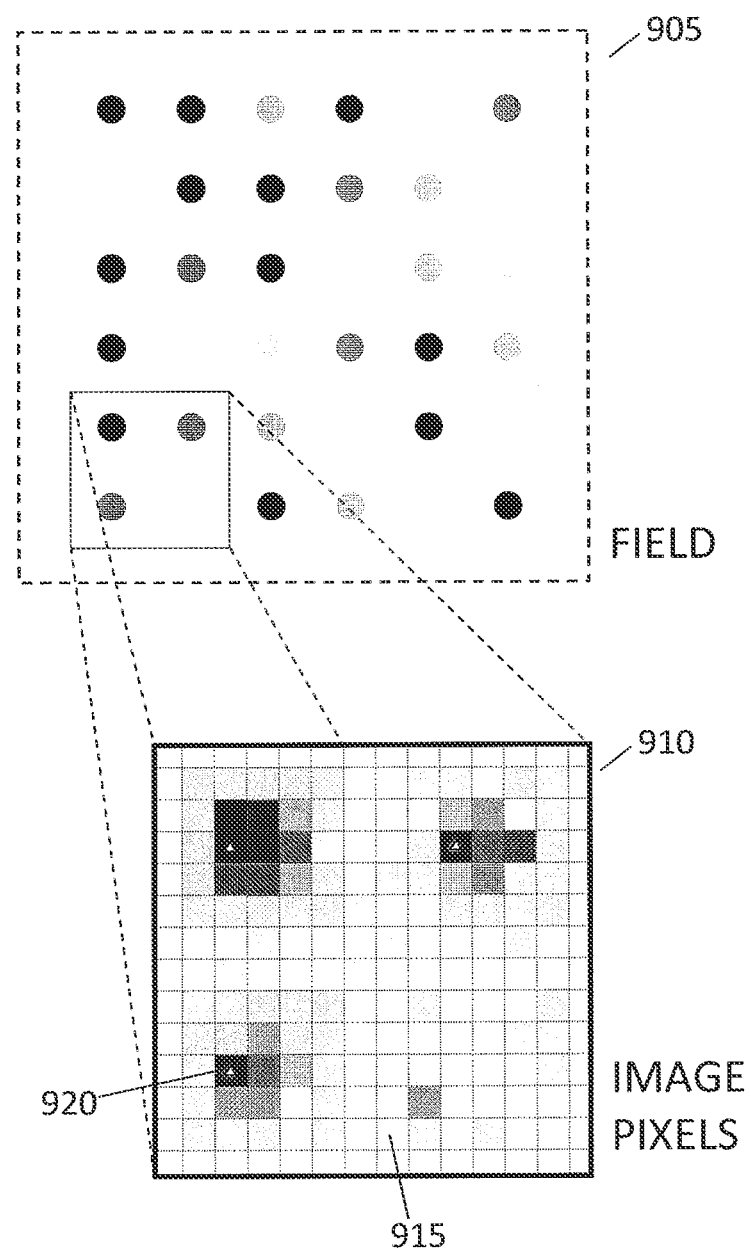
FIG. 12 is a diagram for illustrating imaging of field spots.

FIG. 12 shows a conceptual diagram of imaging field spots. In FIG. 12, several field spots are shown in box 905. The spots have varying brightness; some spots are not emitting any fluorescence at all, while others are bright. In a typical field acquired in a DNA sequencing system, only a quarter or less of the field spots are visible because only one fluorescence color at a time is imaged. Thus, the field may be sparse.

Inset 910 shows a few of the spots as recorded by pixels in an image sensor. Light from a single field spot may be detected in more than one pixel. There is also some background noise—pixels that record greater than zero brightness when there is no emission from the nearest field spot. The first step in the procedure outlined in FIG. 12 is background subtraction, as previously mentioned. One method for background subtraction is to take the brightness recorded by the dimmest pixel in an image and subtract that brightness from every pixel in the image. In inset 910 for example, pixel 915 is the dimmest and its brightness may be subtracted from every pixel in the inset. Background subtraction is usually performed on contiguous blocks of pixels representing a subset of the spots in a field; i.e. not on all the pixels in an image of a field at once.

Once a background level has been subtracted from an image, field spots are detected. One technique is to examine a subset of pixels, say a 5×5 array, and designate that the location of the brightest pixel is the location of a field spot. Another method for detecting field spots is to fit a Gaussian distribution to pixel brightness levels and use the location of the pixel nearest the peak of the best fit distribution. In inset 910, white triangles indicate pixels, such as pixel 920, which have been identified as the location of field spots.

Once field spots have been identified, the process of fitting a grid to the field spots may begin. As a starting point a grid may be established that is aligned with the pixels in an image sensor. Grid fitting involves adjusting the grid to align it as closely as possible with field spots.

Four parameters, rotation, scale (i.e. magnification), and lateral (x and y) offsets of the grid, are adjusted to find a best fit. One may design a grid with more parameters which would permit more precise fitting of astigmatism, distortion, warping and other types of error. These higher order errors are due to factors such as imperfections in lenses, chip substrates or translation stages. These errors are less convenient than rotation, scale and offset to compensate dynamically in an imaging system.

Figure 13A:
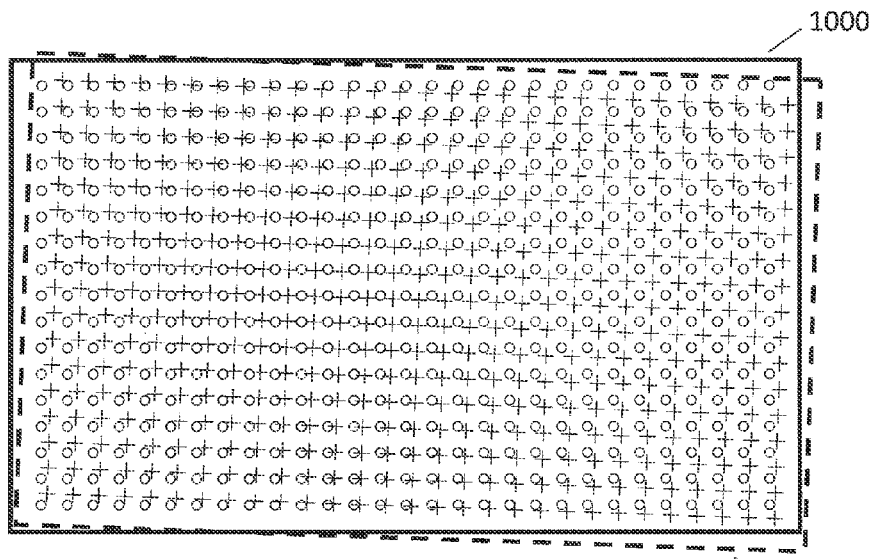
FIG. 13A and FIG. 13B are diagrams showing field and grid patterns before and after alignment.
Figure 13B:
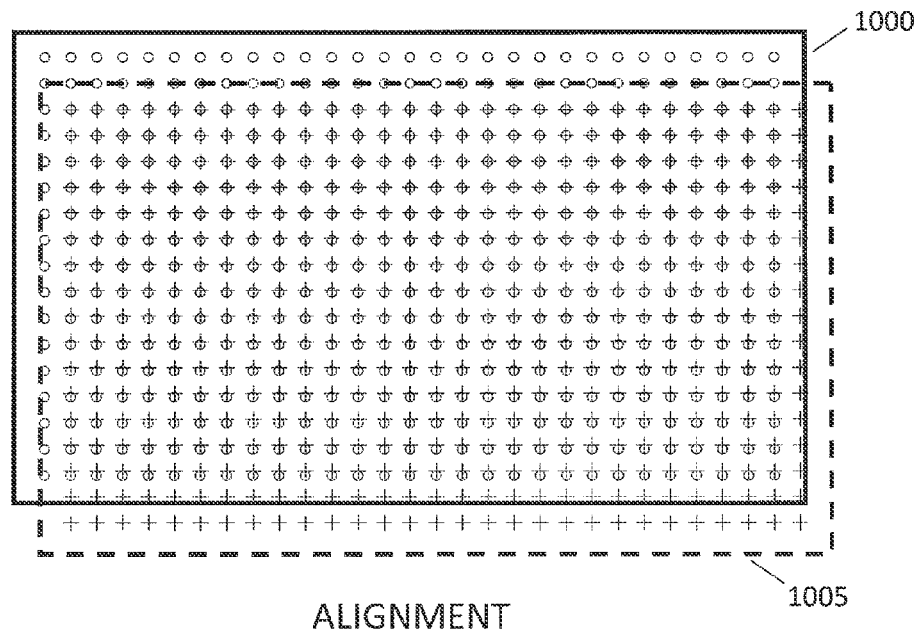

FIG. 13A and FIG. 13B are conceptual diagrams of a field 1000 and a grid 1005 before ("A") and after ("B") two dimensional alignment. After alignment the positions of field spots and grid points substantially match, except for offset errors modulo the grid period. (Translation of a regular grid by distances equal to the grid period leaves the grid unchanged without knowledge of the location of the edges, or equivalently the origin, of the grid. A method for finding the origin or "registering" the grid is described below.)

Grid alignment involves both an iterative, coarse fit procedure and an analytic, fine fit procedure or procedures. The result of the iterative, coarse fit procedure is a fit in which each grid point is closer to the correct field spot than to any other field spot. In FIG. 13, field 1000 and grid 1005 are misaligned in "A" such that grid points are sometimes closer to incorrect field spots than to correct ones. In "B" each grid point is closest to is correct field spot, modulo the grid period.

FIG. 14 is a pseudo code listing of steps in an iterative, coarse grid fit procedure. The steps in box 1100 are a quadruply nested for loop that evaluates a function on a four-dimensional mesh of parameter values. The parameters that are varied are: grid rotation ("θ"), grid magnification or scale ("S"), grid X translation or offset ("X"), and grid Y translation or offset ("Y"). The function, F, which is evaluated at each mesh spot, is the sum of the squared distances between each grid point and the nearest field spot:

$$F = \sum_i |r_{Fi} - r_{Gi}|^2,$$

where the vector $\vec{r_F} r_F$ is the position of a field spot, the vector $r_{Fi}$ is the position of the nearest grid point or reference in a grid, and the sum F is over all field spots.

The value of F is recorded for each (θ, S, X, Y) combination tested. The combination that yields the smallest value of F is the best fit available using this iterative procedure. Finite step sizes $\Delta\theta$, $\Delta S$, $\Delta X$, and $\Delta Y$ affect the length of time required to perform the coarse fit as it takes more time to step through a finer mesh of parameter values. It is unlikely that the coarse fitting procedure yields an optimum fit, as the optimum ($\theta$, S, X, Y) combination almost certainly lies between mesh points. The step ranges, $[\theta_{min}, \theta_{max}]$, $[S_{min}, S_{max}]$, $[X_{min}, X_{max}]$, and $[Y_{min}, Y_{max}]$ are chosen such that a solution in which each grid point is closest to its correct field spot is included in the parameter mesh.

In general, when processing a set of field spots one does not know in advance how many fluorescent signals (e.g., from DNA nanoballs) to look for. Anywhere from just a few percent to fifty percent or more of the field spots may be "lit up." Other pixels, which may appear to represent field spots, may simply be noise. Thus, in the coarse fit procedure, only bright field spots are used. Typically only the brightest 15% of field spots detected are included in coarse fitting, although the particular threshold is a matter of engineering choice.

Figure 15:
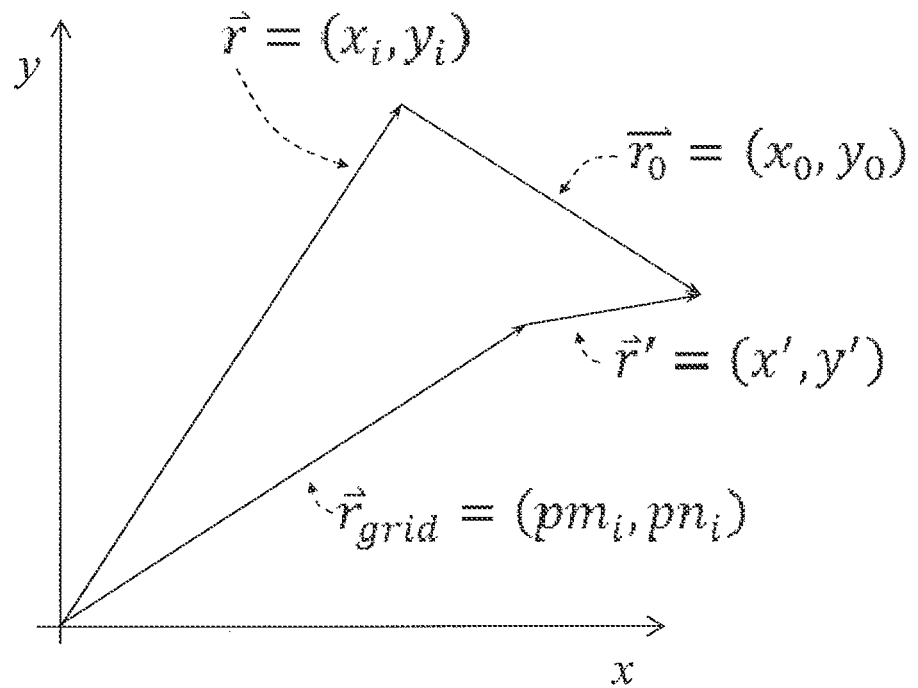
FIG. 15 is a graph showing vectors involved in an analytic, fine grid fit procedure according to the invention.

Once an iterative or coarse fit has been performed, an analytic, fine grid fit procedure optimizes the fit. Conceptually the fine grid fit is equivalent to connecting each grid point (however defined) to the nearest field spot with a rubber band and then allowing the grid to adjust itself. FIG. 15 shows vectors involved in the fine grid fit procedure. In FIG. 15, $r=(x_i, y_i)$ is a field spot while $r_{grid}=(pm_i, pn_i)$ is a grid point of a square grid. Here p is the spacing between grid points (alternately referred to as "pitch", "period", "scale", or "magnification") and $m_i$ and $n_i$ are integer indices that select the grid point nearest to the field spot. The vector $\vec{r}_0=(x_0, y_0)$ is a grid displacement vector, and the vector $\vec{r}'=(x', y')$ is the error between the field and vector the sum of the grid and the grid displacement. The error is related to the field and the displacement by:

$$x'_i = x_i \cos\theta - y_i \sin\theta + x_0 - m_i p,$$

$$y'_i = x_i \sin\theta + y_i \cos\theta + y_0 - n_i p,$$

where $\theta$ represents rotation of the grid with respect to the field around an axis perpendicular to the x-y plane. The goal of the fine fit procedure is to find optimal values for $x_0$, $y_0$, $\theta$ and p that minimize the error between the grid and the field. To find these values, the sum of the squared errors is written as:

$$\chi^2 = \sum_{i=1}^{N} ((x'_i)^2 + (y'_i)^2).$$

where N is the number of field spots. Next, partial derivatives of $\chi^2$ with respect to each of the four independent variables, $x_0$, $y_0$, $\theta$ and p, are set equal to zero, which yields the following set of equations (known as a Jacobian transformation):

$$\begin{bmatrix} -X_i \\ -Y_i \\ M_i X_i + N_i Y_i \\ 0 \end{bmatrix} = \begin{bmatrix} -Y_i & -M_i & N & 0 \\ X_i & -N_i & 0 & N \\ M_i Y_i - N_i X_i & M_i^2 - N_i^2 & -M_i & -N_i \\ X_i^2 + Y_i^2 & M_i Y_i - N_i X_i & -Y_i & X_i \end{bmatrix} \begin{bmatrix} \theta \\ p \\ x_0 \\ y_0 \end{bmatrix}$$

$$\begin{bmatrix} -X_i \\ -Y_i \\ M_i X_i + N_i Y_i \\ 0 \end{bmatrix} = \begin{bmatrix} -Y_i & -M_i & N & 0 \\ X_i & -N_i & 0 & N \\ M_i Y_i - N_i X_i & M_i^2 - N_i^2 & -M_i & -N_i \\ X_i^2 + Y_i^2 & M_i Y_i - N_i X_i & -Y_i & X_i \end{bmatrix} \begin{bmatrix} \theta \\ p \\ x_0 \\ y_0 \end{bmatrix}.$$

Here, small angle approximations $\cos\theta=1$ and $\sin\theta=\theta$ have been used to linearize the equations, and sums are represented according to the conventions:

$$A_i \equiv \sum_{i=1}^{N} a_i$$

$$A_i \equiv \sum_{i=1}^{N} a_i \text{ and}$$

$$A_i B_i \equiv \sum_{i=1}^{N} a_i b_i.$$

The solution of the matrix equation yields $x_0$, $y_0$, $\theta$, and p as required.

Once a first fine grid fit has been obtained, further improvement in the fit may be achieved by peak threshold discrimination followed by an additional fine fit. In the coarse fit and the first pass of the fine fit, only a fraction of the field spots are considered. Usually only the brightest 15% of field spots detected are included in first-pass fine fitting, but the actual percentage is a matter of engineering choice. The reason that only the brightest spots are used in first pass is that many of the dimmer spots may be noise. After coarse and fine fitting however, one may reevaluate which spots to include in a fit via peak threshold discrimination.

Figure 16:
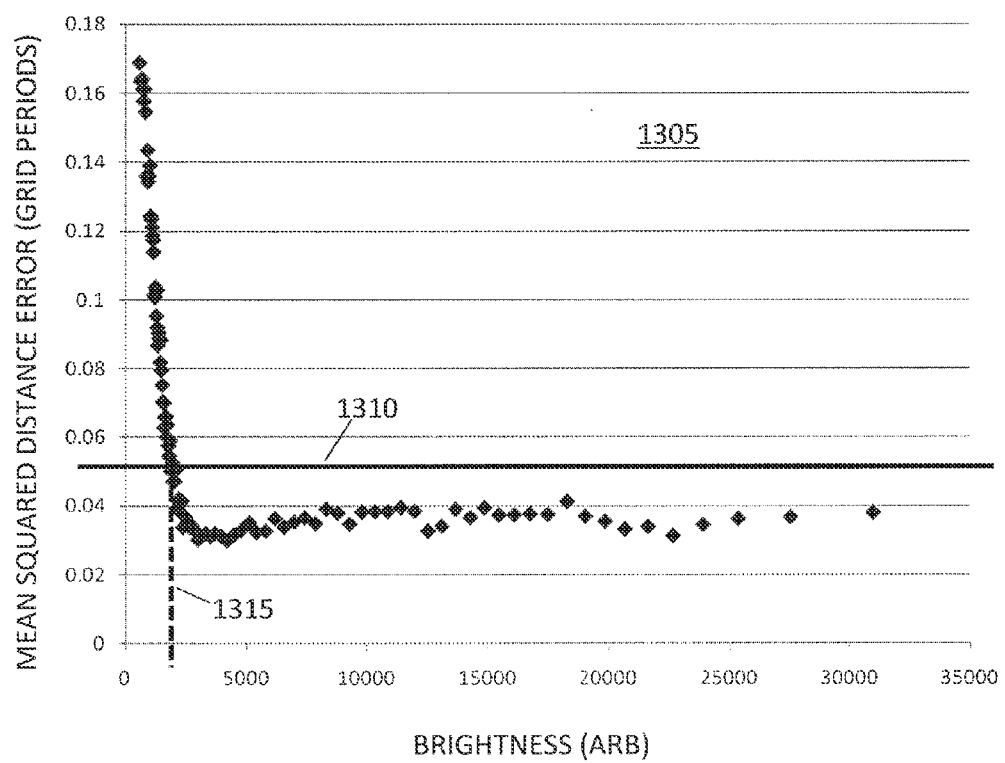
FIG. 16 is a graph showing results of peak threshold discrimination according to the invention.

To establish a useable brightness threshold for including field spots in a fit, all of the field spots, not just those used in initial coarse and fine fitting, are sorted into groups. The groups are, for example, the fifty brightest spots, the next fifty brightest spots, or the first thousand and next thousand, etc. (The number need only be large enough so that the mean squared distance error for all the spots in the group has statistical significance.) Next the groups are plotted on a graph of mean squared distance error versus brightness. FIG. 16 is a graph 1305 of peak threshold discrimination data for a typical field. In FIG. 16, field spots in groups with low mean squared distance error are brighter than those with high mean squared distance errors. The graph has a fairly sharp bend where the mean squared distance error for groups of dimmer spots increase rapidly. A threshold may be drawn near this spot, such as threshold 1310 drawn in FIG. 16. The number of field spots in groups with mean squared distance error smaller than the threshold is usually significantly more than the 15% of the number of field spots used in the coarse and first-pass fine fits. This larger number of field spots may then be used to repeat the fine fit procedure described in connection with FIG. 15. In FIG. 16, for example, all field spots brighter than the dimmest spot under threshold 1310, i.e., those to the right of dashed line 1315, may be included in a second fine fit.

Figure 17A:
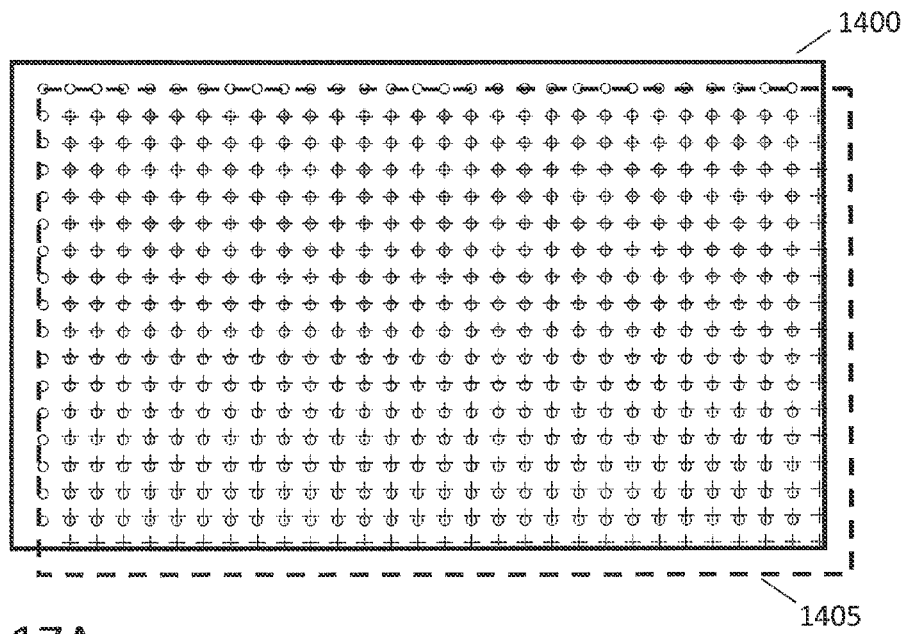
FIG. 17A is a diagram showing a grid aligned but not registered with a field.
Figure 17B:
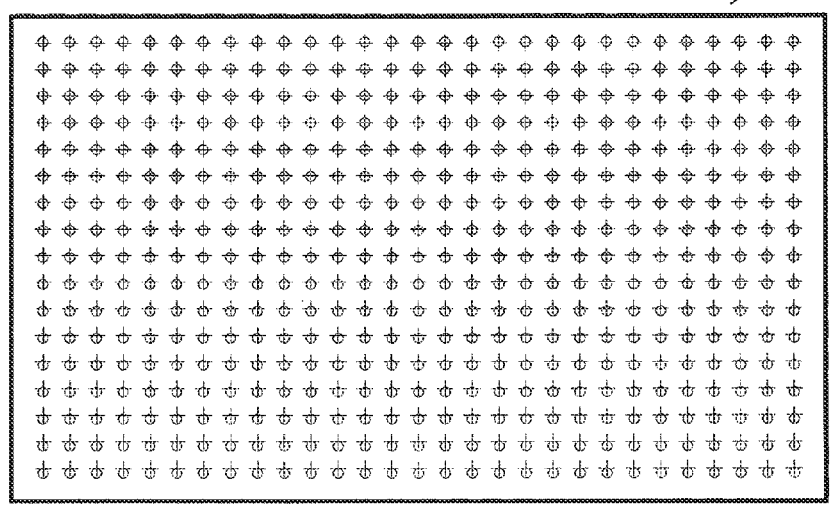
FIG. 17B is a diagram showing a grid aligned and registered with a field.

At this point the grid is aligned as well as it can be to the field of fluorescent spots. The grid may still be offset from the field by integer numbers of grid periods in the X and Y directions. FIG. 17A shows a conceptual diagram of a grid that is aligned with a field, but not yet registered at the proper offset. In FIG. 17A, field 1400 and grid 1405 are aligned, but not registered, at "A." In FIG. 17B, the field 1400 and grid 1405 are properly registered at "B". The alignment and fitting procedures described so far cannot however distinguish between situations "A" and "B" of FIGS. 17A and 17B. Thus an additional registration procedure is necessary.

Figure 18:
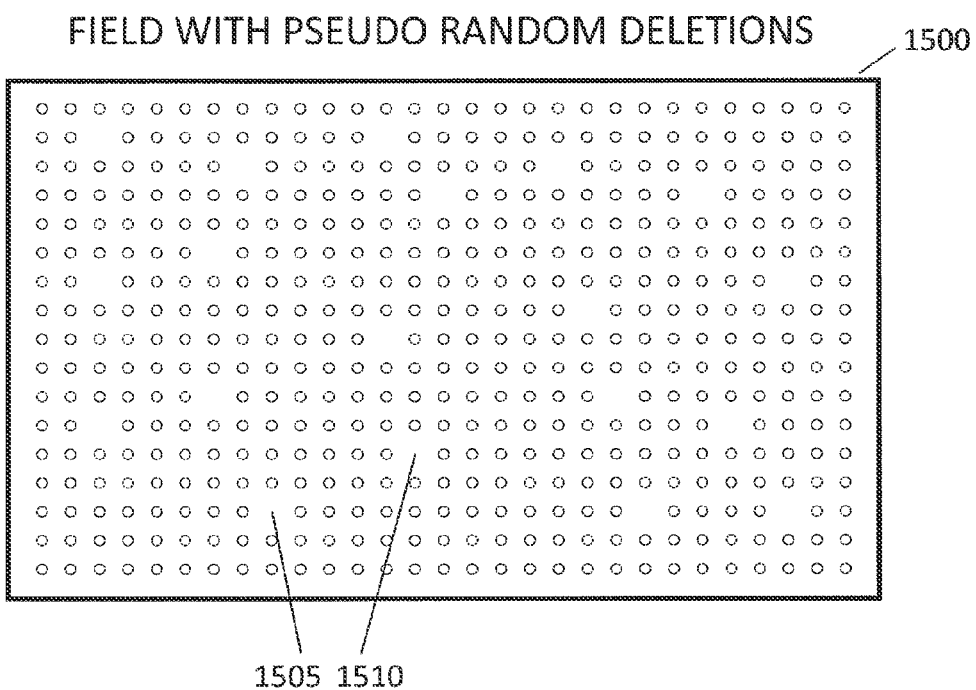
FIG. 18 is a diagram of a field of a chip with deletions at pseudo random locations in accordance with the invention.

Registration according to the invention is efficiently accomplished using a pseudo random deletion pattern of field spots. FIG. 18 shows a conceptual diagram of a two-dimensional field 1500 with a pseudo random deletion pattern according to the invention. It is understood that the array may include billions of sites that support biochemical experiments, such as probe-anchor ligation with DNA nanoballs, and that areas of the substrate other than the surface sites do not support biochemical experiments. Such regions are chemically treated to reduce nonspecific binding of biomolecules. Some of the spots in the field, such as spots 1505 and 1510 are missing, i.e., deleted. Fluorescently tagged biomolecules are unlikely to appear at these spots and therefore knowledge of which spots are missing can be used for accurate registration of the fields to the grid.

Chips for self assembling DNA nanoball arrays may be patterned using semiconductor lithography techniques, as well as direct write e-beam techniques and microcontact printing techniques. Positive amine groups for example may be patterned to bind negative DNA nanoballs in a field array. Deletion of spots in the field array may be accomplished by removing features from the lithography mask(s) used to pattern the amine groups. If the location of a particular field spot has no amine groups, DNA nanoballs are unlikely to attach.

Pseudo random deletion patterns are used for registration by using cross-correlation techniques to match a known "mask" pattern or pseudo random pattern from a field array. If the mask is properly registered with the field, very little light will be seen as the holes are lined up with deleted spots. If the mask is displaced from the field by some number of field periods, light from spots that happen to fall under the holes will pass through the mask. The amount of light passing through the mask will be roughly equal for all displacements, except when the mask and field are registered.

Figure 19:
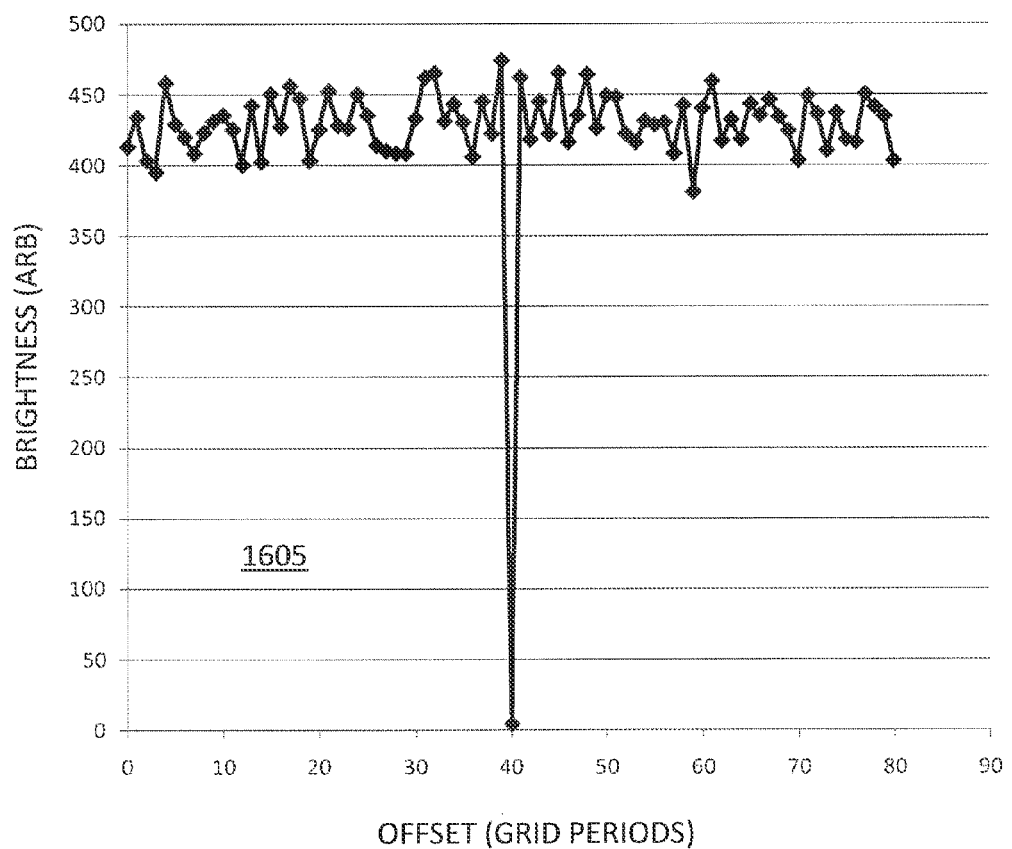
FIG. 19 is a graph showing grid offset data.

FIG. 19 shows an example of grid registration data in graph 1605. The graph shows brightness for offsets from 0 to 81 field periods. These 81 raster pattern offsets are those of a two-dimensional 9 by 9 field of X and Y offsets. For each offset except grid period number 40, the brightness of field spots appearing in the pseudo random pattern is roughly 425 arbitrary brightness units. At offset 40, the brightness is nearly zero. Because of the raster pattern of 81 offset periods, offset 40 refers to X=4, Y=4. This is the offset required to register the grid to the field.

Pseudo random deletion patterns may be used to identify fields as well as to register grid points to field spots. Referring by way of example to FIG. 18, each field is provided with a first pseudo random deletion pattern that is common to all fields and that is used for registration. In addition, each field may also have two further pseudo random deletion patterns: one that identifies the row and one that identifies the column of the specific field on the chip, as indicated in connection with the system of FIG. 6. Thus each observed field pattern is cross correlated against the common pseudo random deletion pattern used for registration and against dozens of other pseudo random deletion patterns to determine where on the chip the field lies. It is desirable that approximately 3% of the field spots be deleted in pseudo random patterns; however as little as a set of patterns comprising just 1% deletion yields acceptable results. A deletion pattern greater than 3% provides only marginal increase in accuracy and consumes usable space, while a deletion pattern of less than 1% risks a potentially unacceptable error in registration.

Figure 20:
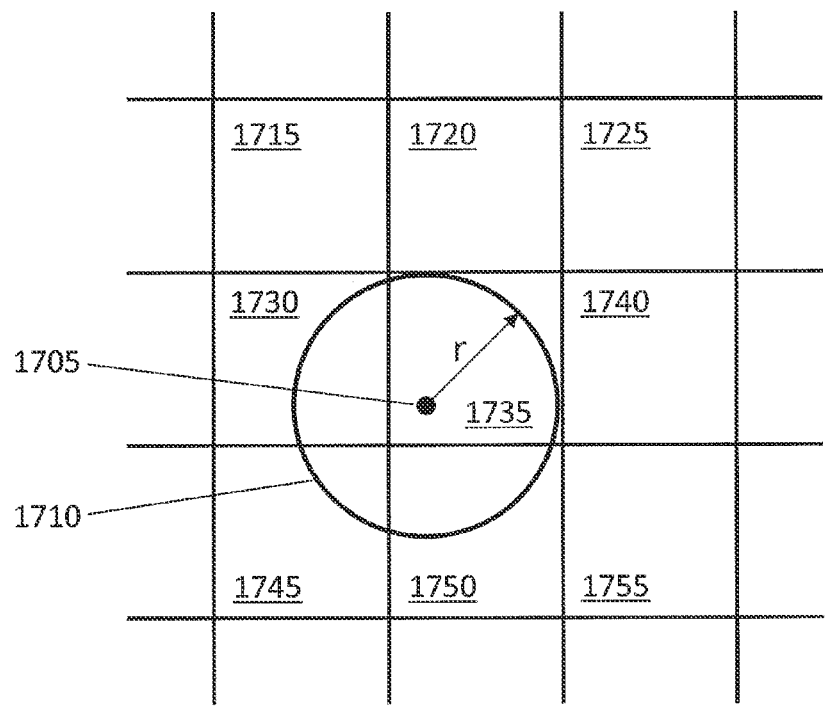
FIG. 20 is a diagram for illustrating sub-pixel grid alignment.

The alignment and registration techniques described here permit rapid and accurate identification of field spots observed in a high density, biochemical array experiment. These techniques allow experiments to be performed on Cartesian-coordinate arrays with fewer pixels per field spot that would otherwise be possible. The position of field spots, as fit to an ideal grid, is determined with sub-pixel accuracy. The brightness of each field spot may therefore be calculated as a weighted average of pixel intensities recorded by pixels near the field spot. FIG. 20 illustrates an example of how sub-pixel grid alignment may be used.

In FIG. 20, a representative 9 by 9 block of pixels (pixels 1715, 1720, 1725, 1730, 1735, 1740, 1745, 1750 and 1755) is shown. The position of field spot 1705 has been determined by the grid alignment and registration techniques described above. Circle 1710 is a conceptual representation of the transverse extent of light emitted from field spot 1705. One may think of circle 1710 as a one-sigma radius of a Gaussian distribution, for example. If the position of field spot 1705 were known with only pixel accuracy one might estimate the brightness of the spot as just the brightness reported by pixel 1735. Or, one might weight the brightness of pixel 1735 50% and the brightness of each of pixels 1720, 1730, 1740 and 1750 12.5% each. Given a high accuracy, sub-pixel estimate of field spot position, however, a more precise weighting is possible in accordance with the invention. In the example of FIG. 20 for example, the weights of pixels 1730, 1735, 1745 and 1750 might be 20%, 50%, 10% and 20% respectively, representing the overlap between each pixel and circle 1710.

Genome studies and other uses of high density biochemical arrays require advanced imaging methods such as those described herein to achieve commercially viable data acquisition rates. High-density ordered-array chips and advanced alignment and registration techniques are key elements of systems that power large-scale human genome studies.

In addition, the devices and machine of the present invention are useful in numerous methods for biochemical interrogation of nucleic acids of unknown sequence. For example, analysis slides of the invention can be used with hybridization-based methods, such as disclosed in U.S. Pat. Nos. 6,864,052; 6,309,824; and 6,401,267 and U.S. Published Patent Application 2005/0191656; sequencing by synthesis methods, such as disclosed in U.S. Pat. No. 6,210,891 6,828,100; 6,833,246; 6,911,345; Ronaghi et al (1998), *Science*, 281: 363-365; and Li et al, *Proc. Natl. Acad. Sci.*, 100: 414-419 (2003); and ligation-based methods, e.g., WO1999019341, WO2005082098, WO2006073504 and Shendure et al. (2005), *Science*, 309: 1728-1739. To the extent permitted by relevant law, the content of these publications are incorporated herein by reference for all purposes.

In particular aspects, multiple analysis slides are used in high throughput analysis with multiple biochemical sequencing reactions. Flow cell type analysis slides may, for example, be arranged side-by-side, or one in front of the other in a sequencing reaction system. The multiple flow cells optionally includes nucleic acids or primers attached to the substrate of the flow cell, either randomly or in a predetermined manner, so that the identity of each nucleic acid in the multiple flow cells can be monitored throughout the reaction processes. The nucleic acids or primers can be attached to the surface such that at least a portion of the nucleic acids or primers are individually optically resolvable.

In one preferred aspect of the embodiments, the flow slides for use in systems of the invention comprise a substrate on which nucleic acids of unknown sequence are immobilized. In certain aspects of the embodiments of the invention, a clamping means is capable of clamping together a plurality of flow cells. Typically, from one to around twelve or sixteen flow cells may be clamped simultaneously by a single clamping means. The flow slides can be arranged in the clamping means in a substantially horizontal or substantially vertical manner, although any position intermediate between these two positions may be possible.

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular aspects and are not limiting to the embodiments shown. Changes in detail or structure may be made without departing from the basic elements of the present technology as defined in the following claims. In the claims of any corresponding utility application, unless the term "means" is used, none of the features or elements recited therein should be construed as means-plus-function limitations pursuant to Title 35 U.S.C. §112 ¶6.

What is claimed is:

1. A method for use in performing biochemical experiments comprising:
   providing a microarray comprising a solid planar substrate having a surface;
   preparing a substrate for imaging to establish location and registration of biochemical sites on the substrate by providing a predetermined two-dimensional spatial pattern of biochemical sites in periodic distance between adjacent sites on the substrate;
   detecting image field spots in a spatial two-dimensional array on the substrate corresponding to biochemical sites in an image on the substrate;
   aligning a spatial two-dimensional grid with image field spots of biochemical sites on the substrate to determine a grid offset in order to permit alignment using Moiré patterns;
   the surface further comprising a regular two-dimensional array of optically resolvable surface sites, the optically resolvable surface sites comprising: (a) attachment sites configured for attachment of biomolecules and (b) sites in a plurality of preselected deletion patterns configured to prevent attachment of the biomolecules, wherein each deletion pattern is configured to cross-correlate to at least one mask pattern,
   capturing an image of the microarray;
   registering the image comprising cross correlating the deletion patterns to the mask pattern to determine absolute location within a field.

2. The method according to claim 1, the deletion patterns being pseudo random.

3. The method of claim 1, the registering step comprising further cross correlating two deletion patterns with two mask patterns.

4. The method of claim 1, the preparing step comprising subtracting a background light level from the image.

5. The method of claim 4, the subtracting step including:
   finding intensity of the dimmest pixel within a defined array of pixels; and subtracting that intensity from each pixel the defined array.

6. The method of claim 1, the image field spots detecting step including choosing the location of a brightest pixel associated with each field spot.

7. The method of claim 1, the aligning step comprising a coarse fitting and a fine fitting.

8. The method of claim 1, the aligning step comprising iteratively testing different combinations of rotation, scale, x-offset, and y-offset to find a tested combination having minimum least squares distances between each grid point and each field spot.

9. The method of claim 1, the aligning step further comprising:
   forming the sum of the squared distances between each image field spot and its corresponding grid point; and
   finding the minimum of the sum by:
      calculating its partial derivatives with respect to rotation, scale, x-offset, and y-offset variables,
      setting the partial derivatives equal to zero, and
      solving the resulting system of linear equations.

10. The method of claim 1, the alignment step including:
    cataloging image field spots by intensity group;
    plotting group average spot brightness versus group average distance from nearest grid points; and
    repeating the fine fitting step on all image field spots in groups for which the group average distance from the nearest grid point is less than a threshold value.

11. The method according to claim 1, wherein the imaging steps are configured to interact with a plurality of different fluorescent labels on molecules at each one of the biochemical sites, the preparing step including:
    obtaining at least one fluorescence-specific image of the substrate for further processing of image data.

12. The method of claim 1, the cross-correlating comprising interacting with a pattern having less than three percent of deleted grid points.

13. The method of claim 1, the cross-correlating comprising interacting with a pattern having less than three percent of deleted grid points.

14. The method of claim 1, the cross-correlating comprising interacting with a pattern having less than three percent of deleted grid points.

15. The method according to claim 1, wherein the imaging steps are configured to interact with a plurality of different fluorescent labels on molecules at each one of the biochemical sites, the preparing step including:
    obtaining at least one fluorescence-specific image of the substrate for further processing of image data.

16. A method for use in performing biochemical experiments comprising:
    providing a solid, planar substrate having an array of sites on which biochemical experiments are performed, the array characterized by a predetermined two-dimensional spatial pattern in periodic distance between adjacent sites;
    observing light emitted by the biochemical experiments using an imaging system having an array of pixels, the array characterized by constant distances between pixels; and
    light emitted by the biochemical experiments being focused in spots on the array of pixels, each said spot corresponding to a biochemical experiment;
    wherein distance between said spots not being an integer multiple of distance between said pixels,
    for observing and identifying the biochemical experiments.

17. The method of claim 16, the biochemical experiments comprising combinatorial probe—anchor ligation with DNA nanoballs.

18. A method for use in performing biochemical experiments comprising:
    providing a solid, planar substrate having discrete surface sites, the surface sites being configured to support biochemical experiments, the sites being located at spots in a predetermined two-dimensional spatial periodic array of spots on a surface of the substrate, and a fraction of the sites that would otherwise exist being deleted from the array according to a preselected deletion pattern;
    performing biochemical experiments at the sites;
    obtaining images of the biochemical experiments at the sites;
    cross-correlating representations of the images with representations of the deletion pattern to determine absolute location of the spots; and
    observing and identifying the images with subpixel accuracy.

19. The method of claim 18, the image observing step comprising weighting contributions of output from adjacent pixels based on exact location of the spots.

20. The method of claim 18, the deletion pattern being pseudo random.

21. The method of claim 18 wherein the fraction is between approximately 1% and approximately 3%.

22. The method of claim 18, areas of the substrate other than said surface sites being chemically treated to reduce non-specific binding of biomolecules.

23. The method of claim 18, the biochemical experiments comprising combinatorial probe-anchor ligation with DNA nanoballs.

24. A system comprising:
    a preprocessor for preparing a planar substrate for imaging to establish location and registration of biochemical sites on the substrate according to a predetermined two-dimensional pattern;
    a detector for detecting image field spots corresponding to biochemical sites in an image on a substrate;
    a first subsystem for aligning a two-dimensional grid with said image field spots; and
    a second subsystem for registering grid points with said image field spots; the registering subsystem including a first cross correlator for cross correlating representations of the image field spots with representations of a first known deletion pattern of image field spots on the substrate to determine absolute location within a two-dimensional field.

25. The system of claim 24, the second subsystem including a second cross correlator for cross correlating the image field spots with a second known deletion pattern identifying absolute location of the field spots on the substrate.

26. The system of claim 24, at least the first known deletion pattern being pseudo random.

27. The system of claim 24, configured for performing biochemical experiments comprising combinatorial probe-anchor ligation with DNA nanoballs.

28. A device for analysis of biomolecules comprising
    a solid planar substrate having a surface, the surface having thereon a regular two-dimensional array of optically resolvable surface sites, the optically resolvable sites comprising:
    (a) attachment sites for attachment of the biomolecules, and
    (b) sites in a preselected known deletion pattern to which the biomolecules do not attach, wherein the deletion pattern is configured to cross-correlate to a mask pattern for registration of the array in order to allow accurate location and analysis of the biomolecules at the attachment sites.

29. The device of claim 28, wherein the deletion pattern is a pseudo random deletion pattern.

30. The device of claim 28, wherein the two-dimensional array comprises between approximately 1% and approximately 3% of the sites in the preselected known deletion pattern.

31. The device of claim 28, wherein the two-dimensional array comprises at least one million surface sites.

32. The device of claim 28 wherein the biomolecules are nucleic acid molecules.

33. The device of claim 32 wherein the biomolecules are DNA nanoballs.

34. The device of claim 32, wherein the analysis of the biomolecules comprises nucleic acid sequencing.

35. The device of claim 34 wherein the array comprises a plurality of fields laid out in linear rows and columns, and each of the fields comprises a common deletion pattern that is the same for all fields and row/column deletion patterns that identify the row and column of such field.

36. The method of claim 16, wherein nucleic acid molecules are attached to said array of sites, the biochemical experiments comprising sequencing the nucleic acid molecules.

* * * * *